United States Patent
Goehring et al.

(10) Patent No.: US 6,410,540 B1
(45) Date of Patent: Jun. 25, 2002

(54) INHIBITORS OF P38-αKINASE

(75) Inventors: R. Richard Goehring, Pipersville, PA (US); Gregory R. Luedtke, Sunnyvale, CA (US); Babu J. Mavunkel, Sunnyvale, CA (US); Sarvajit Chakravarty, Sunnyvale, CA (US); Sundeep Dugar, Bridgewater, NJ (US); George F. Schreiner, Los Altos Hills, CA (US); David Y. Liu, Palo Alto, CA (US); John A. Lewicki, Los Gatos, CA (US)

(73) Assignee: Scios, Inc., Sunnyvale, CA (US)

( * ) Notice: Subject to any disclaimer, the term of this patent is extended or adjusted under 35 U.S.C. 154(b) by 0 days.

(21) Appl. No.: 09/385,494

(22) Filed: Aug. 27, 1999

Related U.S. Application Data

(60) Provisional application No. 60/125,343, filed on Mar. 19, 1999, and provisional application No. 60/098,219, filed on Aug. 28, 1998.

(51) Int. Cl.⁷ .................. A61K 31/50; A61K 31/495; A61K 31/445
(52) U.S. Cl. .................. 514/252.13; 514/254.09; 514/330
(58) Field of Search .................. 514/330, 252.13, 514/254.09

(56) References Cited

U.S. PATENT DOCUMENTS

| | | | |
|---|---|---|---|
| 5,663,346 A | 9/1997 | Buzzetti et al. | |
| 5,719,135 A | 2/1998 | Buzzetti et al. | |

FOREIGN PATENT DOCUMENTS

| | | |
|---|---|---|
| WO | WO94/20062 | 9/1994 |
| WO | WO95/06032 | 2/1995 |
| WO | WO96/22976 | 8/1996 |
| WO | WO96/40143 | 12/1996 |
| WO | WO97/26252 | 7/1997 |
| WO | WO98/06715 | 2/1998 |
| WO | WO98/07425 | 2/1998 |
| WO | WO98/28292 | 7/1998 |
| WO | WO 99 61426 | 12/1999 |

OTHER PUBLICATIONS

Beak, P., et al., "The Tertiary Amide as an Effective Director of Ortho Lithiation," J. Org. Chem., (1982) 47:34–46.
Bindal, R.D., et al., Steric Factors in Amide–Directed Metalations of N,N–Dialkyl–6–methoxynaphthalene–2–carboxamides: Synthesis of a Sterically Perturbed Acylnaphthol, J. Org. Chem., (1987) 52(15):3181–5.
Eyers, P.A., et al., "Conversion of SB 203580–Insensitive MAP Kinase Family Members to Drug–Sensitive Forms by a Single Amino–Acid Substitution," Chemistry & Biology, (1998) 5:321–8.
Gschwend, H.W., et al., "Heteroatom–Facilitated Lithiations," Org. Rxns., (1979) 26:1–360.

Hansch, C., et al., "'Aromatic' Substituent Constants for Structure–Activity Correlations," J. Med. Chem. (1973) 16(11):1207–16.
Jiang, Y., et al., Characterization of the Structure and Function of a New Mitogen–Activated Protein Kinase (p38β), J. Biol. Chem., (1996) 271:17920–6.
Kumar, S., et al., "Novel Homologues of CSBP/p38 MAP Kinase: Activation, Substrate Specificity and Sensitivity to Inhibition by Pyridinyl Imidazoles," Biochem. Biophys. Res. Comm., (1997) 235:533–8.
Li, Z., et al., "The Primary Structure of p38γ: A New Member of p38 Group of MAP Kinases," Biochem. Biophys. Res. Comm., (1996) 228:334–40.
Mavunkel, B.J., "Synthesis and Characterization of Pseudopeptide Bradykinin B2 Receptor Antagonists Containing the 1,3,8–Triazaspiro[4.5]decan–4–one Ring System," J. Med. Chem. (1996), 39(16):3169–73.
Stein, B., et al., "p38–2, a Novel Mitogen–Activated Protein Kinase with Distinct Properties," J. Biol. Chem., (1997) 272:19509–17.
Wang, X.S., et al., "Molecular Cloning and Characterization of a Novel p38 Mitogen–Activated Protein Kinase," J. Biol. Chem., (1997) 272(96):23668–74.
Wang, Y., et al., "Cardiac Muscle Cell Hypertrophy and Apoptosis Induced by Distinct Members of the p38 Mitogen–Activated Protein Kinase Family," J. Biol. Chem., (1998) 273(4):2161–8.

*Primary Examiner*—William R. A. Jarvis
(74) *Attorney, Agent, or Firm*—Morrison & Foerster LLP

(57) ABSTRACT

The invention is directed to methods to treat conditions mediated by p38-αkinase using compounds of the formula (1)

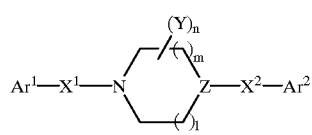

and the pharmaceutically acceptable salts thereof, or a pharmaceutical composition thereof,
wherein
Z is N or CR¹, R¹ is a noninterfering substituent,
each of X¹ and X² is a linker,
Ar¹ and Ar² are identical or different, and represent optionally substituted C1–C20 hydrocarbyl residues wherein at least one of Ar¹ and Ar² is an optionally substituted aryl group, with the proviso that when X² is CH₂ or an isostere thereof, X¹ is CO or an isostere thereof, and Ar² is optionally substituted phenyl, Ar¹ is other than an optionally substituted indolyl, benzimidazolyl or benzotriazolyl substituent, and wherein said optionally substituted phenyl is not an optionally substituted indolyl, benzimidazolyl, or benzotriazolyl,
Y is a noninterfering substituent, wherein n is an integer from 0–4, and
wherein m is an integer from 0–4 and l is an integer from 0–3.

25 Claims, No Drawings

INHIBITORS OF P38-α KINASE

This application claims priority to provisional application Nos. 60/125,343, filed Mar. 19, 1999 and 60/098,219, filed Aug. 28, 1998.

TECHNICAL FIELD

The invention is directed to compounds that are useful in treating inflammation and that contain N-containing heterocycles such as piperazine or piperidine moieties coupled to phenyl and other aryl groups. More particularly, the invention concerns novel compounds of this type as well as methods to treat heart and kidney conditions using these and other compounds.

BACKGROUND ART

A large number of chronic and acute conditions have been recognized to be associated with perturbation of the inflammatory response. A large number of cytokines participate in this response, including IL-1, IL-6, IL-8 and TNF. It appears that the activity of these cytokines in the regulation of inflammation rely at least in part on the activation of an enzyme on the cell signaling pathway, a member of the MAP kinase family generally known as p38 and alternatively known as CSBP and RK. This kinase is activated by dual phosphorylation after stimulation by physiochemical stress, treatment with lipopolysaccharides or with proinflammatory cytokines such as IL-1 and TNF. Therefore, inhibitors of the kinase activity of p38 are useful antiinflammatory agents.

PCT applications WO98/06715, WO98/07425, WO98/28292 and WO 96/40143, all of which are incorporated herein by reference, describe the relationship of p38 kinase inhibitors with various disease states. As mentioned in these applications, inhibitors of p38 kinase are useful in treating a variety of diseases associated with chronic inflammation. These applications list rheumatoid arthritis, rheumatoid spondylitis, osteoarthritis, gouty arthritis and other arthritic conditions, sepsis, septic shock, endotoxic shock, Gram-negative sepsis, toxic shock syndrome, asthma, adult respiratory distress syndrome, stroke, reperfusion injury, CNS injuries such as neural trauma and ischemia, psoriasis, restenosis, cerebral malaria, chronic pulmonary inflammatory disease, silicosis, pulmonary sarcosis, bone resorption diseases such as osteoporosis, graft-versus-host reaction, Crohn's Disease, ulcerative colitis including inflammatory bowel disease (IBD) and pyresis.

The above-referenced PCT applications disclose compounds which are p38 kinase inhibitors said to be useful in treating these disease states. These compounds are either imidazoles or are indoles substituted at the 3- or 4-position with a piperazine or piperidine ring linked through a carboxamide linkage. Additional compounds which are conjugates of piperazines with indoles are described as insecticides in WO97/26252, also incorporated herein by reference.

U.S. Pat. No. 5,719,135 describes tyrosine kinase inhibitors containing piperidine or piperazine rings linked through a methylene at position 1 of piperidine to various aromatic systems which must further contain a γ lactam fused to a pyridine ring. Similar compounds are described in U.S. Pat. No. 5,663,346 and in WO096/22976. Other cyclic tyrosine kinase inhibitors are described in PCT application WO095/06032. In addition, WO094/20062 describes balanoids as protein kinase C inhibitors. The balanoid compounds contain multiple aromatic systems which include at least a ring containing at least seven members. Some of the compounds useful in the method of the present invention are known compounds.

DISCLOSURE OF THE INVENTION

The invention is directed to methods of treating inflammation generally, including specific conditions such as those described in the Background section above. The compounds of the invention have been found to inhibit p38 kinase and are thus useful in treating diseases mediated by this enzyme. These compounds also inhibit p38α preferentially as compared to their inhibition of p38β as is further discussed below.

The compounds useful in the invention are of the formula

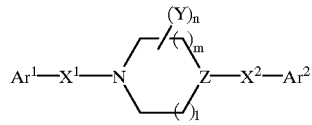

(1)

and the pharmaceutically acceptable salts thereof, or a pharmaceutical composition thereof, wherein Z is N or $CR^1$, $R^1$ is a noninterfering substituent, each of $X^1$ and $X^2$ is a linker, $Ar^1$ and $Ar^2$ are identical or different, and represent optionally substituted C1–C20 hydrocarbyl residues wherein at least one of $Ar^1$ and $Ar^2$ is an optionally substituted aryl group, with the proviso that when $X^2$ is $CH_2$ or an isostere thereof, $X^1$ is CO or an isostere thereof, and $Ar^2$ is optionally substituted phenyl, $Ar^1$ is other than an optionally substituted indolyl, benzimidazolyl or benzotriazolyl substituent, and wherein said optionally substituted phenyl is not an optionally substituted indolyl, benzimidazolyl, or benzotriazolyl, Y is a noninterfering substituent, wherein n is an integer from 0–4, and wherein m is an integer from 0–4 and 1 is an integer from 0–3.

Preferably, the compounds useful in the invention are of the formula

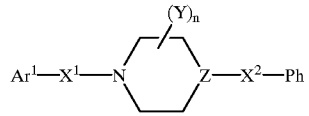

(2)

and the pharmaceutically acceptable salts thereof, wherein $Ar^1$ is optionally substituted furanyl, thiophenyl, phenyl system having 0, 1, or 2 heterocyclic N atoms or naphthyl system having 0, 1, 2 or 3 heterocyclic N atoms;

$X^1$ is CO or an isostere thereof;

Y is optionally substituted alkyl (1–6C), optionally substituted aryl (6–10C), or optionally substituted arylalkyl (7–11C);

n is 0 or 1;

Z is CH or N;

$X^2$ is $CH_2$ or an isostere thereof; and

Ph is optionally substituted phenyl.

The optional substituents on the aryl moieties (including phenyl) include halo, nitro, optionally substituted alkyl (1–6C) or alkenyl (1–6C), CN, guanidino or $CF_3$, as well as RCO, COOR, CONR$_2$, SO$_2$NR$_2$, —OOCR, —NROCR, —NROCOR, NR$_2$, OR or SR, wherein R is H or alkyl (1–6C), as well as substitution by phenyl, itself optionally substituted by the foregoing substituents. Any two substituents may form a 5–7 membered carbocyclic or heterocyclic ring subject to the proviso.

Thus, in one aspect, the invention is directed to compounds of the formulas set forth above and to pharmaceutical compositions containing them. In other aspects, the invention is directed to methods of treatment using compounds of the formula set forth above. The invention is also directed to specific classes of compounds within the genus of formula (1). In other aspects, the invention is directed to methods to produce the classes of compounds useful in the invention.

Modes of Carrying Out the Invention

The compounds of formula (1) set forth above are defined by the nature of the substituents on the heterocycloalkyl ring in the center of the formula. Piperazine or piperidine rings are preferred and piperidine rings are more preferred. The central piperazine or piperidine ring can be expanded or contracted using —CH$_2$ groups so that it includes from 4 members up to 11 members. The substitution on this ring is on the N or Z positions only. Although not bound by this theory, the function of the central heterocycloalkyl group is apparently to space the Ar$^2$ group, which is generally hydrophobic, from the Ar$^1$ group, which is preferably but not necessarily hydrophilic.

The central heterocycloalkyl ring can include from 1–2 N. If the ring contains only 1 N then Z is a —CR$^1$ wherein R$^1$ is a noninterfering substituent. Preferably, R$^1$ is alkyl, alkoxy, aryl, arylalkyl, aryloxy, heteroaryl, halogen, acyl, carboxy, or hydroxy. More preferably, R$^1$ is hydroxy, alkyl, or alkoxy.

The linker that couples the central heterocycloalkyl ring and the Ar$^1$ and Ar$^2$ groups on either end of the molecule are preferably saturated or unsaturated alkylene optionally containing 1–4 carbonyl, 1–4 SO$_2$, and/or 1–3 heteroatoms, including a linker which is CO, SO$_2$, SO or contains a heteroatom, and optionally substituted with a substituent selected from the group consisting of halo, alkyl, alkoxy, cycloalkyl, aryl, aryloxy, arylalkyl, haloalkyl, polyhaloalkyl, haloalkoxy, polyhaloalkoxy, cycloheteroalkyl, cycloheteroalkylalkyl, heteroaryl, heteroarylalkyl, heteroaryloxy, arylthio, arylsulfinyl, arylsulfonyl, heteroarylthio, heteroarylsulfinyl, heteroarylsulfonyl, alkylaminocarbonyl, arylaminocarbonyl, heteroarylaminocarbonyl, alkoxycarbonyl, aryloxycarbonyl, heteroaryloxycarbonyl, acyl, aminocarbonyl, arylcarbonyl, heteroarylcarbonyl, cyano, carboxy, hydroxy, tetrazolyl, imidazole, oxazole, triazole, and —SOR wherein R is hydroxy, alkyl, aryl, alkoxy, aryloxy, cycloalkyl, heteroaryl, heteroarylalkyl, heteroaryloxy, heteroarylalkoxy or cycloheteroalkylalkoxy.

Preferably the linker is a methylene group, a carbonyl group, a methylene group coupled to a carbonyl group, a methylene group having a methyl substituent or a methylene group containing an optionally substituted phenyl group. The alkylene group is C1–C8, and preferably C1–C4, and more preferably C1. Preferably, haloalkyl or polyhaloalkyl groups are CF$_3$ or CF$_3$CH$_2$ and haloalkoxy or polyhaloalkoxy groups are CF$_3$O or CF$_3$CH$_2$O.

Ar$^1$ or Ar$^2$ is an aryl group which is the residue of an aromatic hydrocarbon containing one or more rings optionally including one or more heteroatoms, selected from the group of O, N and S. Preferably the aryl group has 6–12 carbon atoms and up to 3 heteroatoms, and more preferably the aryl group has 6–8 carbon atoms and 1 or 2 heteroatoms. More preferably, the aryl group is a saturated or unsaturated 5–7 membered heterocycle and even more preferably a saturated or unsaturated 5–6 membered heterocycle. Most preferably, the aryl group is phenyl or residues of an optionally benzo-fused heterocycle containing up to 3 heteroatoms selected from S, N and O. The most preferable aryl groups are indolyl, isoquinolyl, quinolyl, benzimidazolyl, benzotriazolyl, benzothiazolyl, benzofuranyl, pyridyl, thienyl, furyl, pyrrolyl, thiazolyl, oxazolyl, imidazolyl, morpholinyl or piperidyl. When the linker is not CO or an isostere thereof, Ar$^1$ or Ar$^2$ is most preferably indolyl, benzimidazolyl or benzotriazolyl.

Ar$^1$ and Ar$^2$ and/or other aryl substituents are optionally substituted with substituents including one or more of halo, alkyl, alkoxy, cycloalkyl, aryl, aryloxy, arylalkyl, haloalkyl, polyhaloalkyl, haloalkoxy, polyhaloalkoxy, cycloheteroalkyl, cycloheteroalkylalkyl, heteroaryl, heteroarylalkyl, heteroaryloxy, arylthio, arylsulfinyl, arylsulfonyl, heteroarylthio, heteroarylsulfinyl, heteroarylsulfonyl, alkylaminocarbonyl, arylaminocarbonyl, heteroarylaminocarbonyl, alkoxycarbonyl, aryloxycarbonyl, heteroaryloxycarbonyl, acyl, aminocarbonyl, arylcarbonyl, heteroarylcarbonyl, cyano, carboxy, hydroxy, tetrazolyl, imidazole, oxazole, triazole, and —SOR wherein R is hydroxy, alkyl, aryl, alkoxy, aryloxy, cycloalkyl, heteroaryl, heteroarylalkyl, heteroaryloxy, heteroarylalkoxy or cycloheteroalkylalkoxy. Preferably the substituents include halo, alkoxy, alkoxyaryl, aminoalkyl, aminoaryl, and substituted aryl. Most preferably Ar$^1$ and Ar$^2$ include at least one halo, alkoxy, or N-containing substituent.

Y is selected from the group consisting of H, optionally substituted alkyl, alkoxy, cycloalkyl, cycloheteroalkyl, aryl, cycloheteroalkyl, heteroaryl, halogen, alkylaminocarbonyl, arlyaminocarbonyl, heteroarylaminocarbonyl, acyl, carboxy, hydroxy, aminocarbonyl, arylcarbonyl, heteroarylcarbonyl, cyano, amino, and alkylamino. Preferred groups are hydroxy, alkyl and carbonyl.

The compounds of formula (2) set forth above are defined by the nature of the substituents on the piperazine or piperidine ring. Piperidine rings are preferred.

In formula (2), Ar$^1$ is optionally substituted furanyl, thiophenyl, optionally substituted phenyl systems having 0, 1, or 2 heterocyclic N atoms or naphthyl systems having 0, 1, 2 or 3 heterocyclic N atoms. The nature of the substituents and the preferred substituents are discussed below.

X$^1$ is CO or an isostere thereof. Thus, in addition to CO, X$^1$ may be CH$_2$, SO, SO$_2$, or CHOH. CO is preferred.

Z is CH or N.

X$^2$ is CH$_2$ or an isostere thereof

The aryl moieties represented by Ar$^1$ and Ph in formula (2) may optionally be substituted by substituents including straight or branched chain alkyl (1–6C), straight or branched chain alkenyl (2–6C), halo, RCO, COOR, CONR$_2$, SO$_2$NR$_2$, —OOCR, —NROCR, —NROCOR, OR, SR, NR$_2$, NO$_2$, CN, or CF$_3$, wherein R is H or straight or branched chain alkyl (1–6C). Phenyl moieties may also be substituted with an additional phenyl residue, preferably at the 4-position. Any two substituents may form a 5–7 membered carbocyclic or heterocyclic ring subject to the proviso. The additional phenyl residue may itself be substituted with the substituents set forth above. The additional phenyl may be substituted in all five positions, but preferably less, preferably in 1–2 positions or not at all.

Preferred substituents include halo, alkyl (1–6C), OR, SR and $NR_2$, more preferably halo, OR and alkyl (1–4C), most preferably halo and $OCH_3$. The substituents on the phenyl moiety as an embodiment of $Ar^1$ or on Ph may occupy all five available positions, preferably 1–2 positions or the phenyl is unsubstituted If $Ar^1$ comprises a pyridyl residue, only 4 positions are available; preferably only 1–2 positions are substituted or preferably the pyridyl is unsubstituted. If $Ar^1$ comprises furanyl or thiophenyl, only 3 positions are available; preferred numbers of substitutions in this case are 1 or 0.

n may be 0 or 1, and is preferably 0. However, when n is 1, Y is present and may be alkyl, arylalkyl or aryl, all of which may optionally be substituted by the substituents set forth above. Preferred embodiments of Y include unsubstituted alkyl (1–6C) and unsubstituted arylalkyl (7–11C), most preferably unsubstituted lower alkyl (1–4C).

The compounds of formula (1) or (2) may be supplied in the form of their pharmaceutically acceptable acid-addition salts including salts of inorganic acids such as hydrochloric, sulfuric, hydrobromic, or phosphoric acid or salts of organic acids such as acetic, tartaric, succinic, benzoic, salicylic, and the like. If a carboxyl moiety is present on the compounds of formula (1) or (2), the compound may also be supplied as a salt with a pharmaceutically acceptable cation.

In the event the compounds of formula (1) or (2) contains one or more chiral centers, all of the stereoisomers are included within the scope of the invention, as well as mixtures thereof Thus, the compounds of formula (1) or (2) in these instances may be supplied as a single stereoisomer, as a racemic mixture, as a partially racemic mixture, or generally, a mixture of stereoisomers in any proportion.

The invention is directed, in addition to methods of treatment, to compounds falling within the scope of formula (1) or (2) as compositions of matter.

In particular, the invention is directed to compounds of the general formula (2), and the pharmaceutically acceptable salts thereof, wherein $Ar^1$ is optionally substituted furanyl, thiophenyl, phenyl system containing 0, 1 or 2 N as heterocyclic atoms or naphthyl system containing 0 1, 2 or 3 N as heterocyclic atoms, $X^1$ is CO or an isostere thereof; Y is optionally substituted alkyl (1–6C), optionally substituted aryl (6–10C), or optionally substituted arylalkyl (7–11C); n is 1; Z is N or CH; $X^2$ is $CH_2$ or an isostere thereof; and Ph is optionally substituted phenyl.

The invention is also directed to compounds of formula (2) and the pharmaceutically acceptable salts thereof, wherein $Ar^1$ is optionally substituted furanyl, thiophenyl, phenyl system containing 1 or 2 N atoms as heterocyclic atoms or naphthyl system containing 0, 1, 2, or 3 N atoms as heterocyclic atoms, $X^1$ is CO or an isostere thereof; Y is optionally substituted alkyl (1–6C), optionally substituted aryl (6–10C), or optionally substituted arylalkyl (7–11C); n is 0–1; Z is N or CH; $X^2$ is $CH_2$ or an isostere thereof; and Ph is optionally substituted phenyl; wherein said substituents on $Ar^1$ and Ph are independently selected from the group consisting of straight or branched chain alkyl (1–6C), straight or branched chain alkenyl (2–6C), halo, RCO, COOR, $CONR_2$, $SO_2NR_2$, —OOCR, —NROCR, —NROCOR, OR, SR, $NR_2$, $NO_2$, CN, or $CF_3$, wherein R is H or straight or branched chain alkyl (1–6C).

The invention is also directed to a compound of the formula (2) and the pharmaceutically acceptable salts thereof, wherein $Ar^1$ is an ortho substituted furanyl, thiophenyl, phenyl system containing 0, 1 or 2 N as heterocyclic atoms, or naphthyl system containing 0, 1, 2 or 3 N as heterocyclic atoms; said ortho substituent is straight or branched chain alkyl (1–6C), straight or branched chain alkenyl (2–6C), halo, RCO, COOR, $CONR_2$, $SO_2NR_2$, —OOCR, —NROCR, —NROCOR, OR, SR, $NR_2$, $NO_2$, CN, or $CF_3$, wherein R is H or straight or branched chain alkyl (1–6C), with the proviso that when said $Ar^1$ is phenyl and said ortho substituent is OR, either R must be alkyl (3–6C) or $Ar^1$ must be

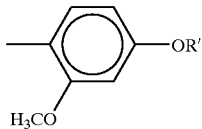

where R' is H, alkyl (1–6C), alkenyl (2–6C) or arylalkyl (7–12C);

$X^1$ is CO or an isostere thereof, Y is optionally substituted alkyl (1–6C), optionally substituted aryl (6–10C), or optionally substituted arylalkyl (7–11C); n is 0–1; Z is N or CH; and Ph is optionally substituted phenyl.

The ortho position is defined herein as the position in the ring adjacent the $X^1$ position, for example the 2-position in a 5-membered ring.

Preferred embodiments of the compounds of the invention are as described above with respect to compounds useful in the invention methods. In particular piperidine forms are preferred over piperazines.

Particularly preferred compounds of the invention include:

1-(2-methoxy-4-hydroxybenzoyl)-4-benzylpiperidine;

1-(2-methoxy-4-methoxybenzoyl)-4-benzylpiperidine;

1-(2-methoxy-4-benzyloxybenzoyl)-4-benzylpiperidine; and 1-(2-methoxy-4-methoxybenzoyl)-4-(4-fluorobenzyl) piperidine.

In addition, the following table illustrates preferred compounds of the invention.

| Compound # | Structure |
|---|---|
| 1 | 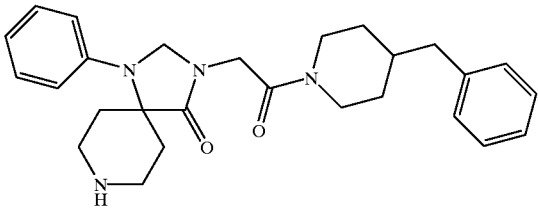 |
| 2 | 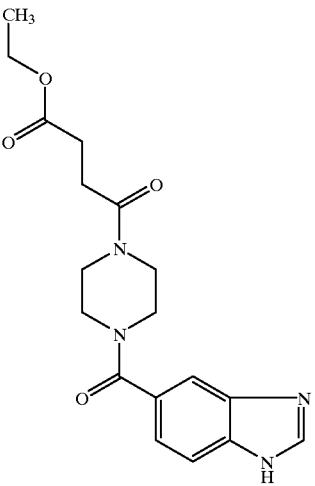 |
| 3 | 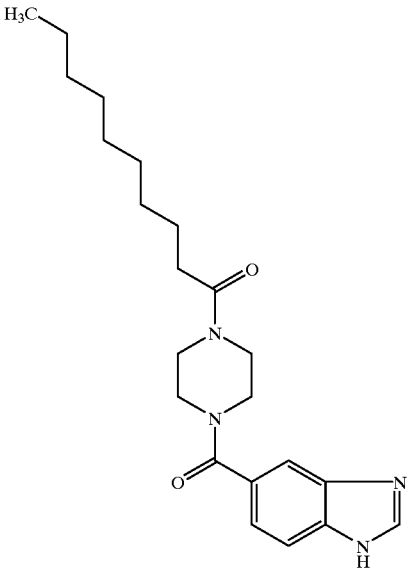 |

-continued
| Compound # | Structure |
|---|---|
| 4 | 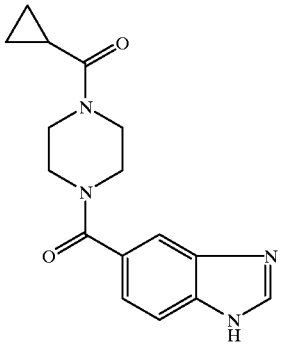 |
| 5 | 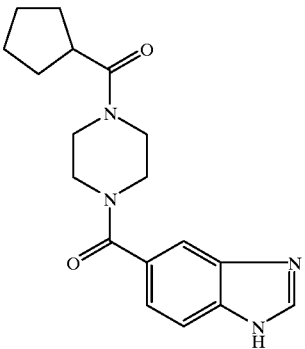 |
| 6 | 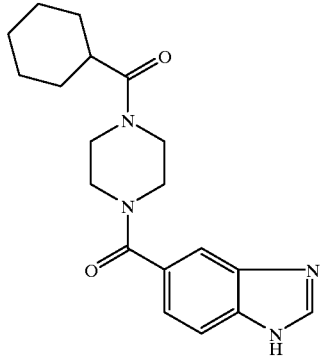 |
| 7 | 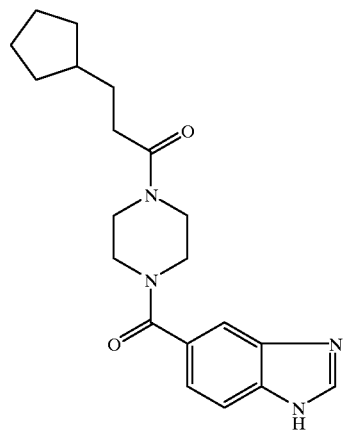 |

-continued
| Compound # | Structure |
|---|---|
| 8 | 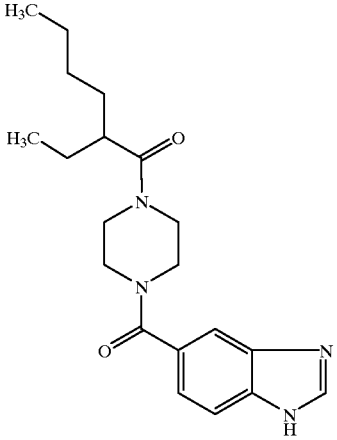 |
| 9 | 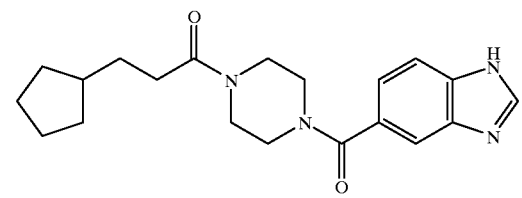 |
| 10 | 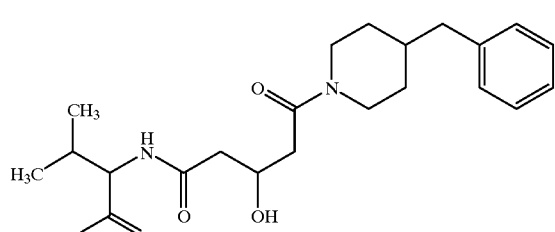 |
| 11 | 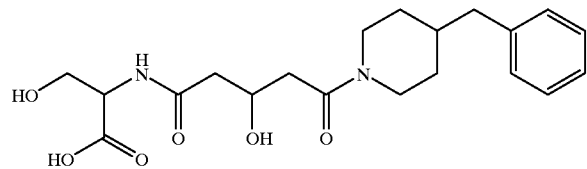 |
| 12 | 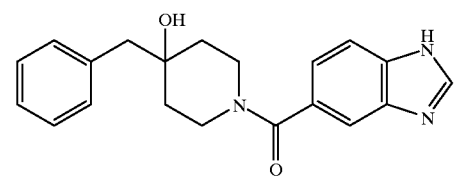 |

-continued
| Compound # | Structure |
|---|---|
| 13 | 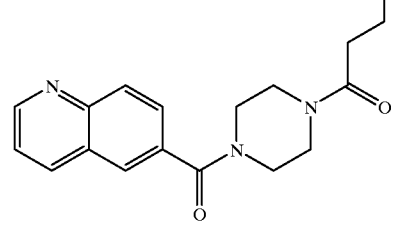 |
| 14 | 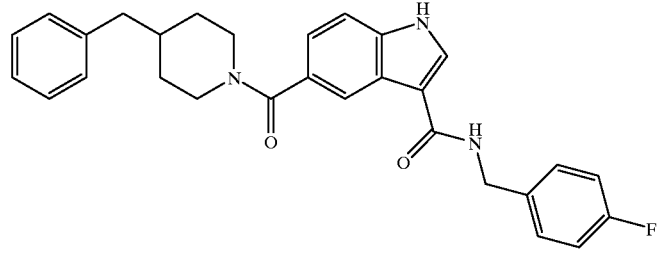 |
| 15 | 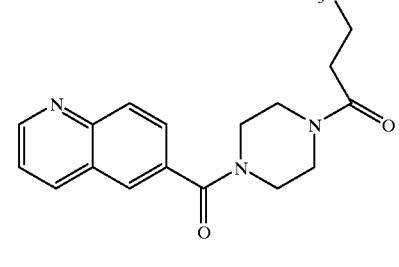 |
| 16 | 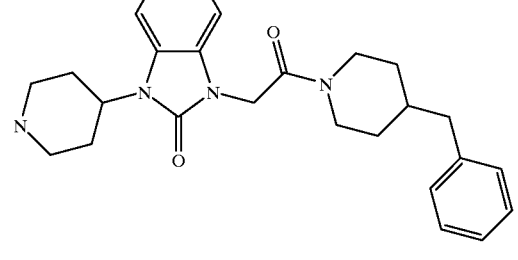 |
| 17 | 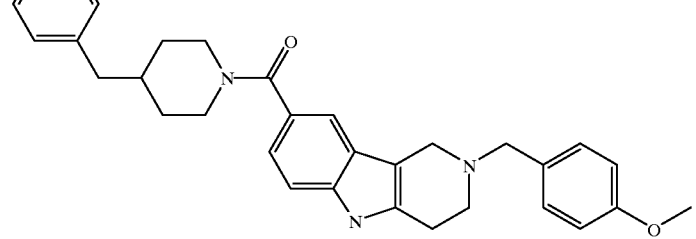 |

-continued
| Compound # | Structure |
|---|---|
| 18 | 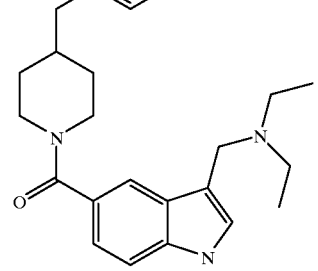 |
| 19 | 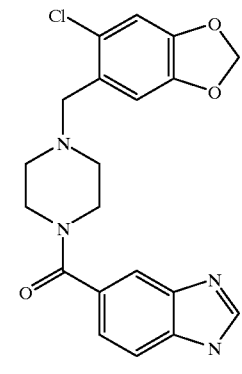 |
| 20 | 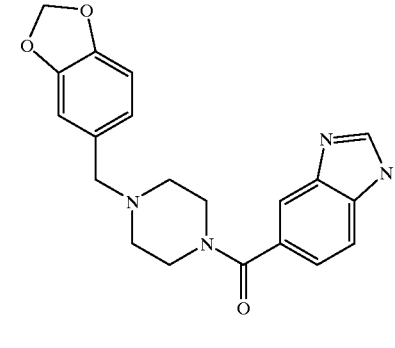 |
| 21 | 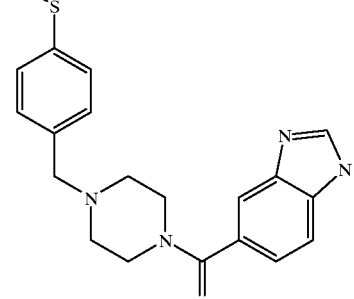 |

-continued
| Compound # | Structure |
|---|---|
| 22 | 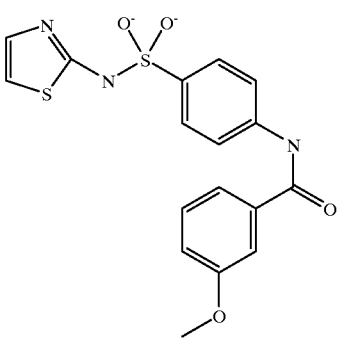 |
| 23 | 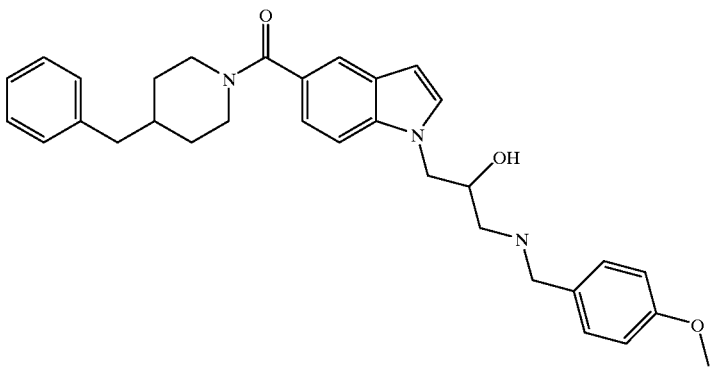 |
| 24 | 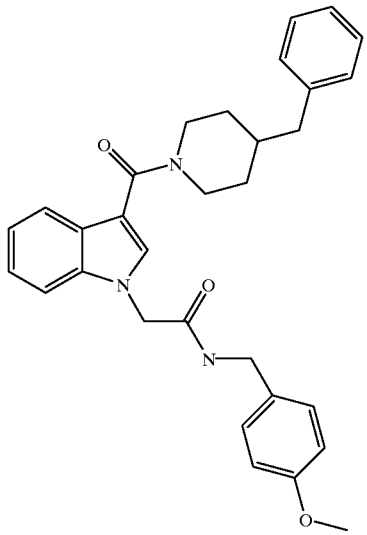 |

-continued
| Compound # | Structure |
|---|---|
| 25 | 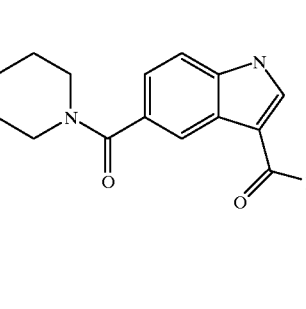 |
| 26 | 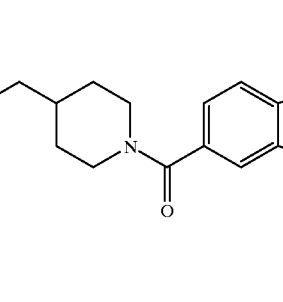 |
| 27 | 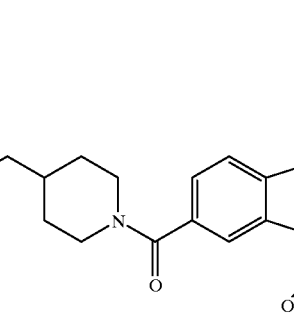 |
| 28 | 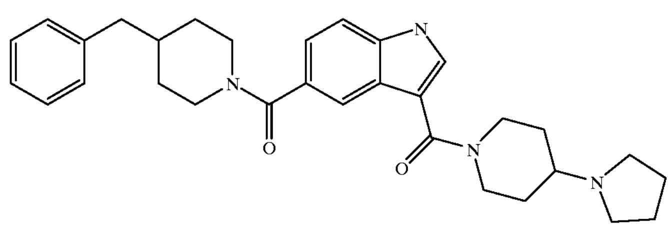 |

-continued
| Compound # | Structure |
|---|---|
| 29 | 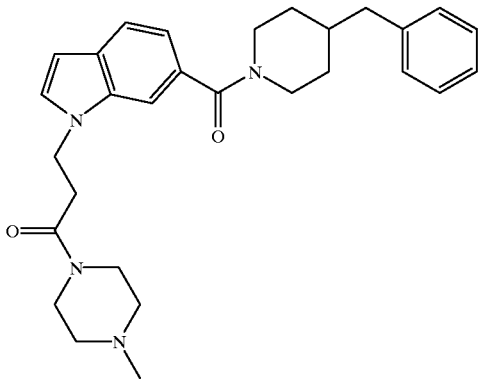 |
| 30 | 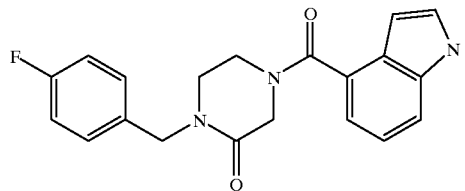 |
| 31 | 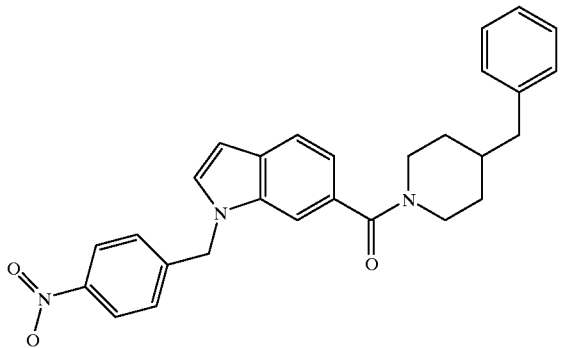 |
| 32 | 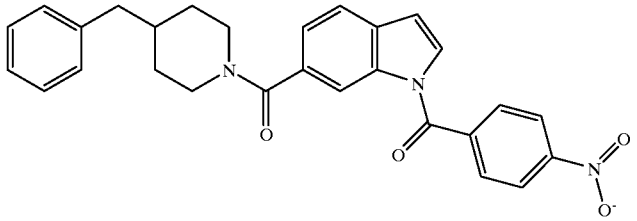 |

-continued

| Compound # | Structure |
|---|---|
| 33 | 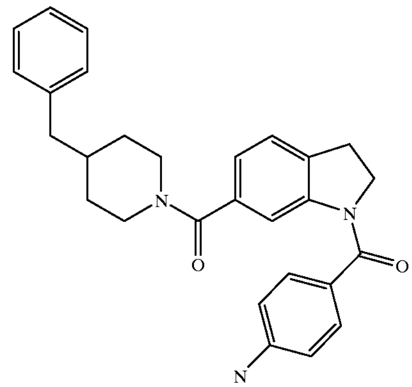 |
| 34 | 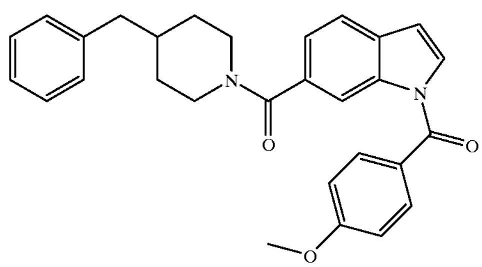 |
| 35 | 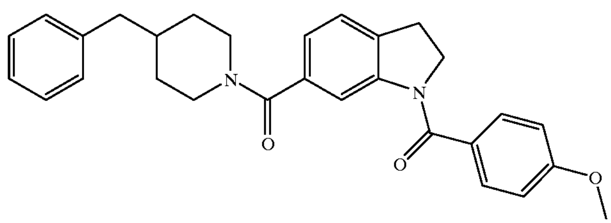 |
| 36 | 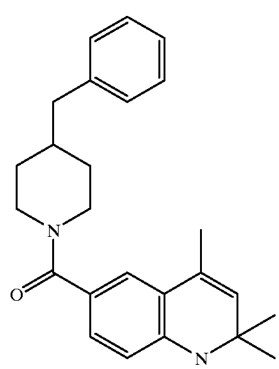 |
| 37 | 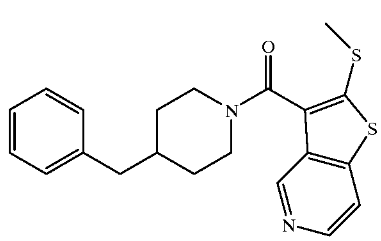 |

-continued
| Compound # | Structure |
|---|---|
| 38 | 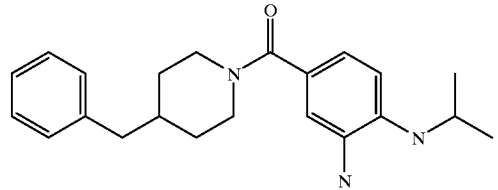 |
| 39 | 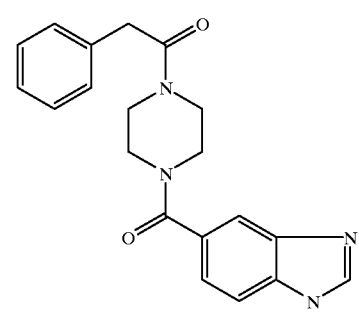 |
| 40 | 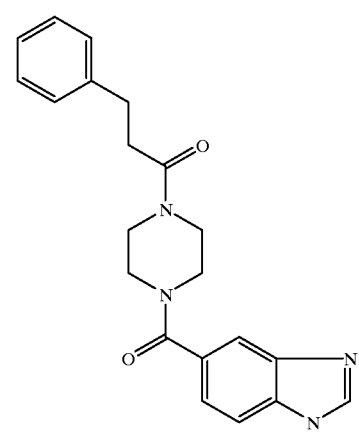 |
| 41 | 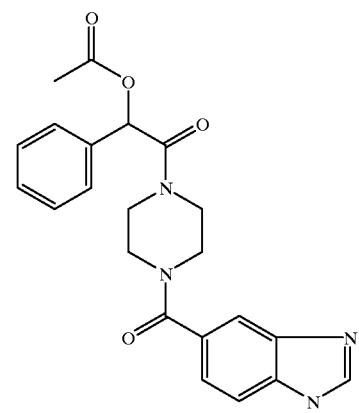 |

-continued
| Compound # | Structure |
|---|---|
| 42 | 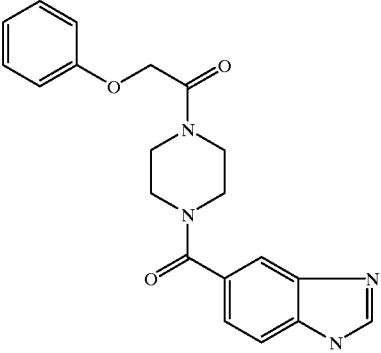 |
| 43 | 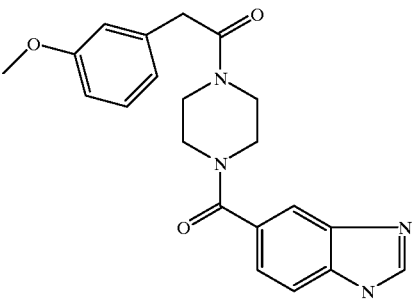 |
| 44 | 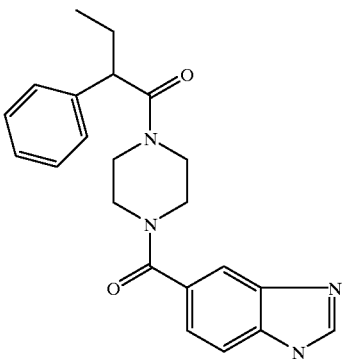 |
| 45 | 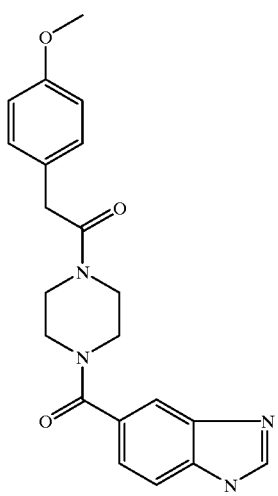 |

-continued
| Compound # | Structure |
|---|---|
| 46 | 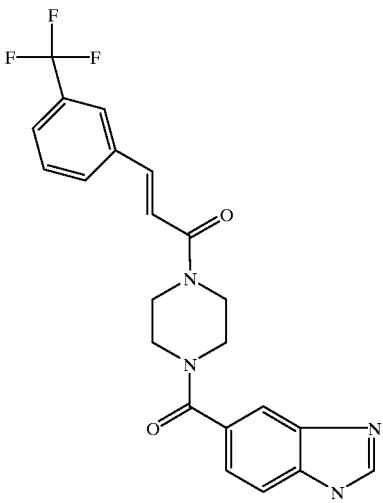 |
| 47 | 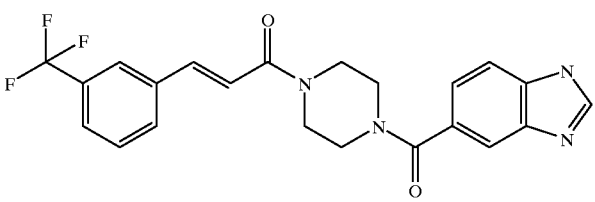 |
| 48 | 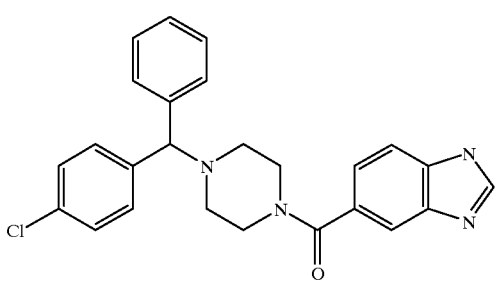 |
| 49 | 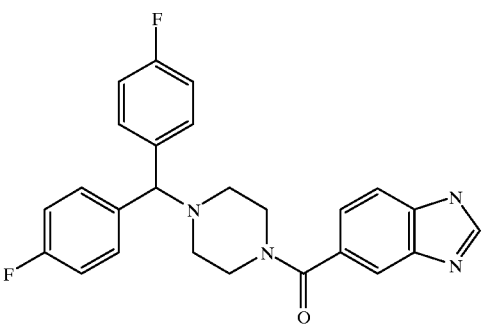 |

-continued

| Compound # | Structure |
|---|---|
| 50 | (structure) |
| 51 | (structure) |
| 52 | (structure) |
| 53 | (structure) |
| 54 | (structure) |

-continued

| Compound # | Structure |
|---|---|
| 55 | 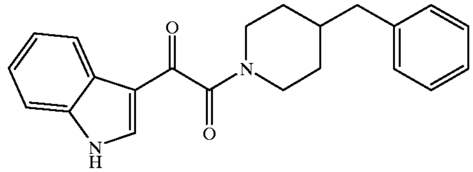 |
| 56 | 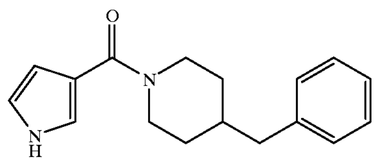 |
| 57 | 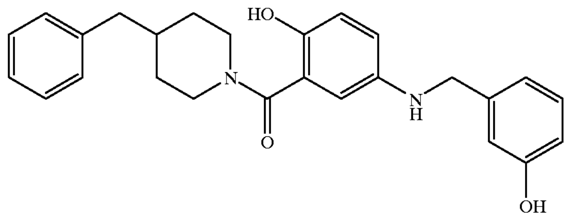 |
| 58 | 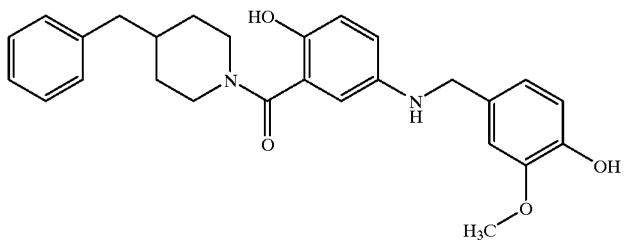 |
| 59 | 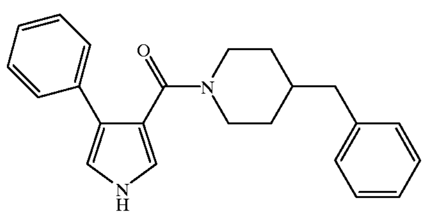 |
| 60 | 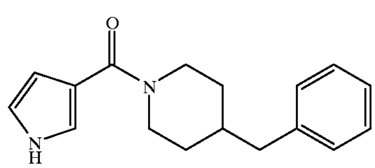 |
| 61 | 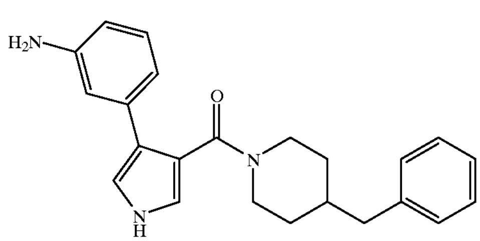 |

-continued
| Compound # | Structure |
|---|---|
| 62 | 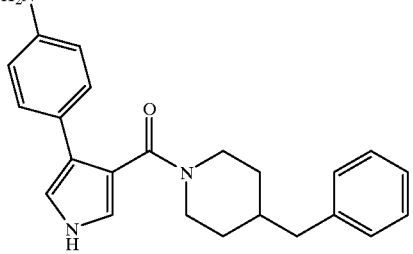 |
| 63 | 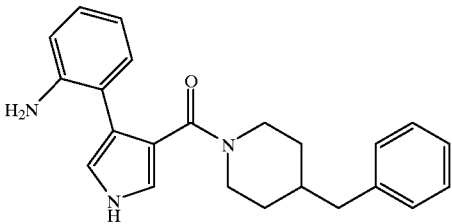 |
| 64 | 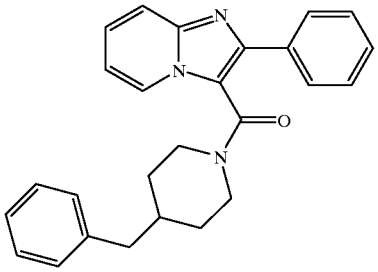 |
| 65 | 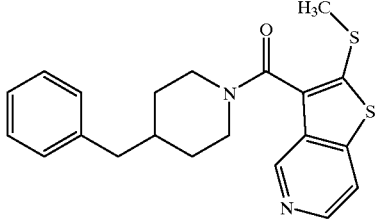 |
| 66 | 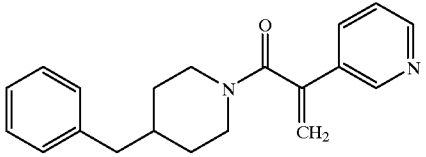 |
| 67 | 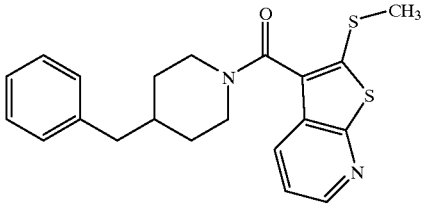 |

-continued

| Compound # | Structure |
|---|---|
| 68 | 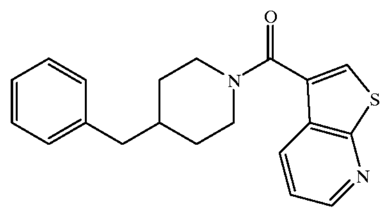 |
| 69 | 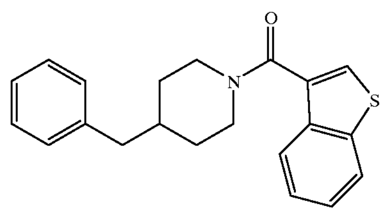 |
| 70 | 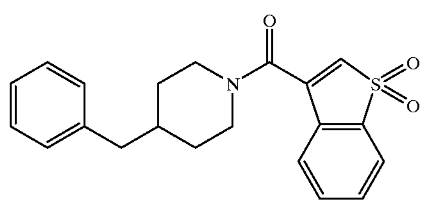 |
| 71 | 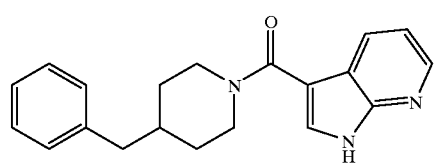 |
| 72 | 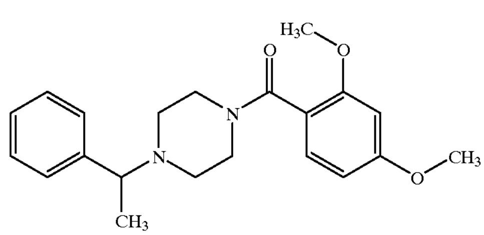 |
| 73 | 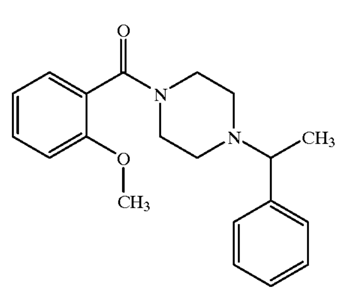 |

-continued
| Compound # | Structure |
|---|---|
| 74 | 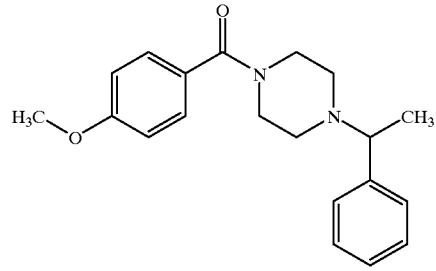 |
| 75 | 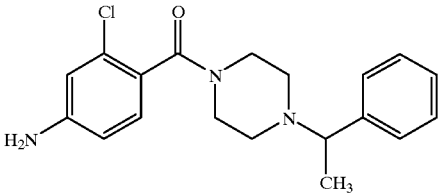 |
| 76 | 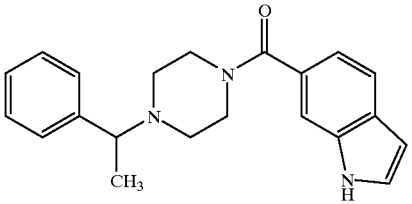 |
| 77 | 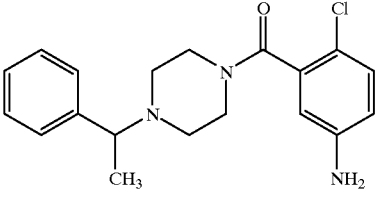 |
| 78 | 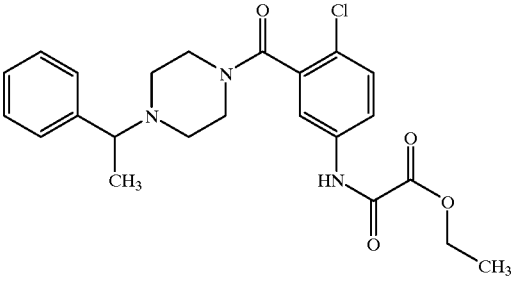 |
| 79 | 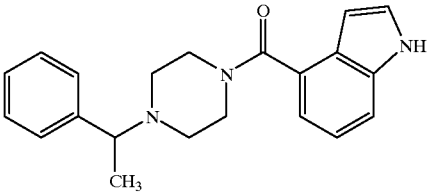 |

-continued

| Compound # | Structure |
|---|---|
| 80 | 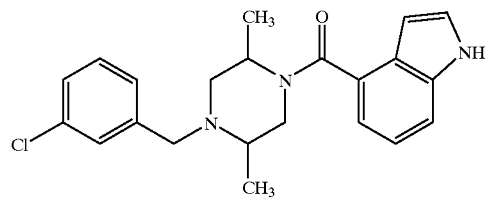 |
| 81 | 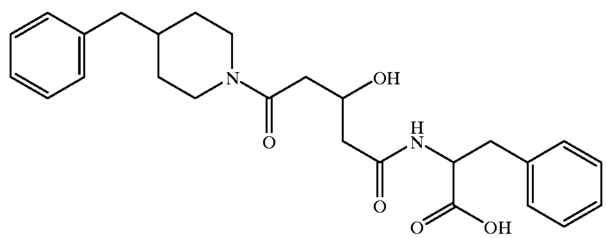 |
| 82 | 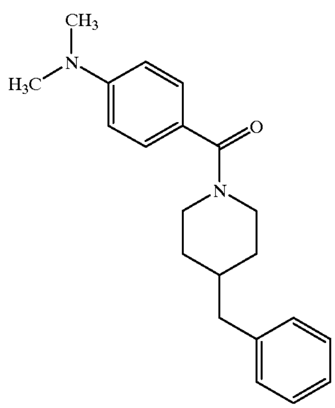 |
| 83 | 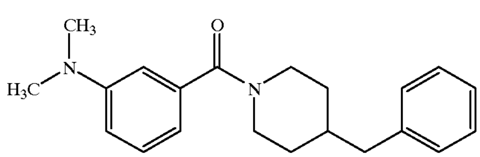 |
| 84 | 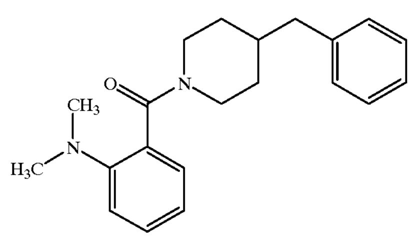 |
| 85 | 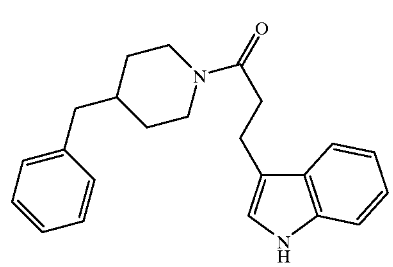 |

-continued

| Compound # | Structure |
|---|---|
| 86 | 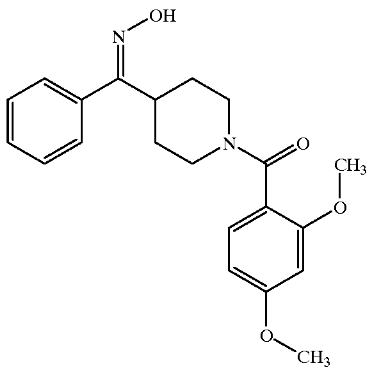 |
| 87 | 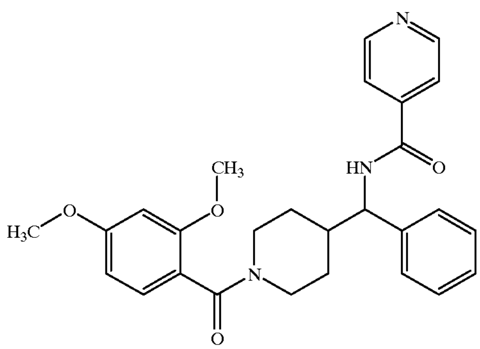 |
| 88 | 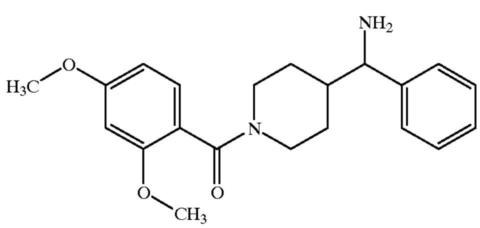 |
| 89 | 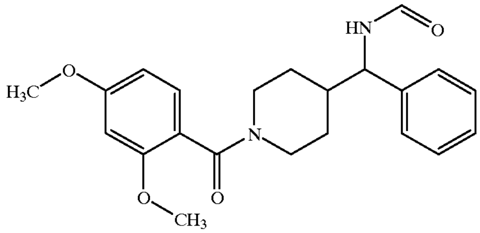 |
| 90 | 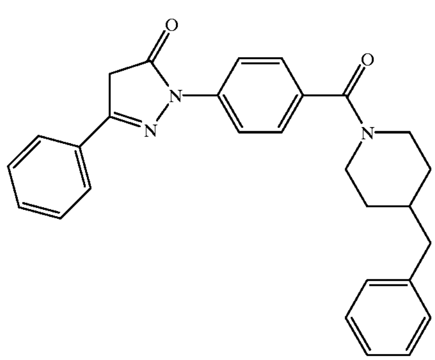 |

-continued
| Compound # | Structure |
|---|---|
| 91 | 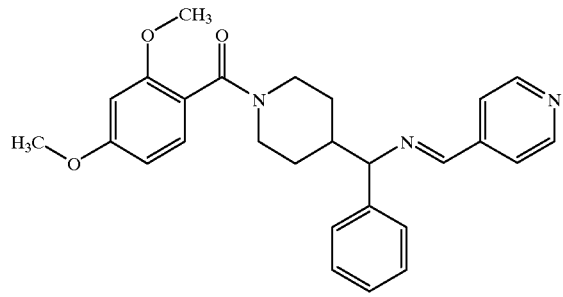 |
| 92 | 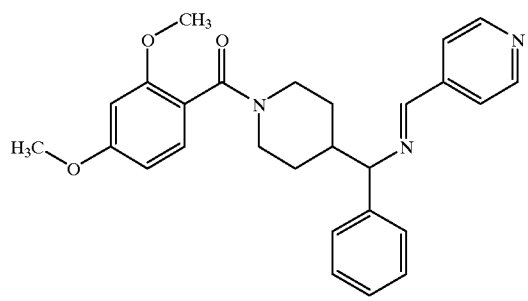 |
| 93 | 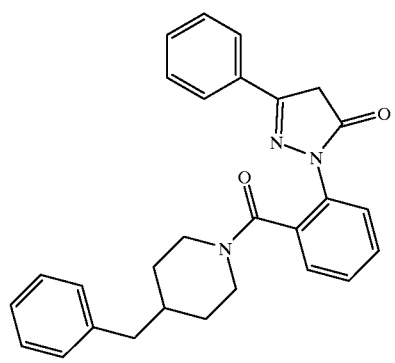 |
| 94 | 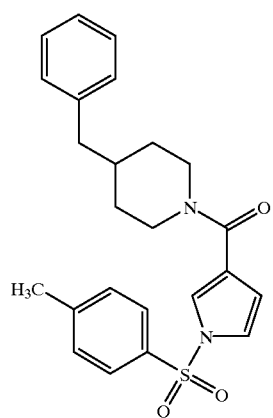 |

-continued

| Compound # | Structure |
|---|---|
| 95 | 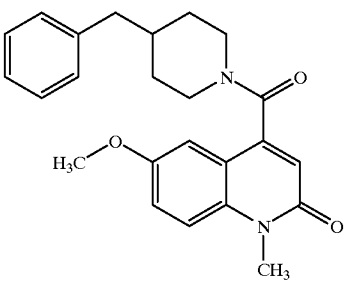 |
| 96 | 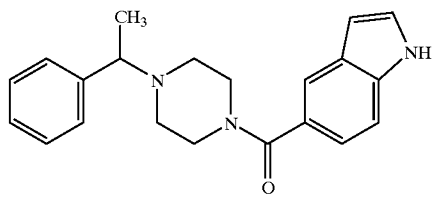 |
| 97 | 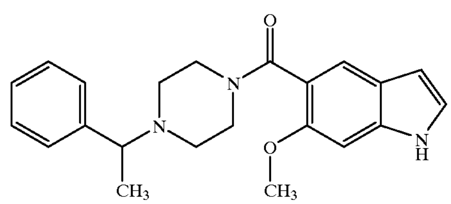 |
| 98 | 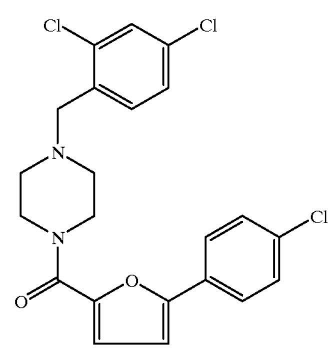 |
| 99 | 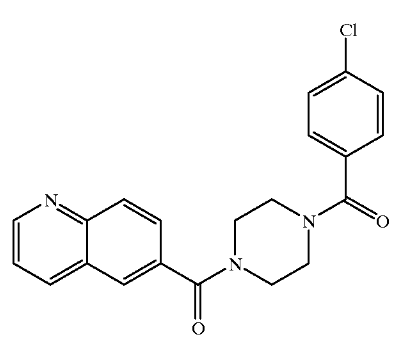 |

-continued
| Compound # | Structure |
|---|---|
| 100 | 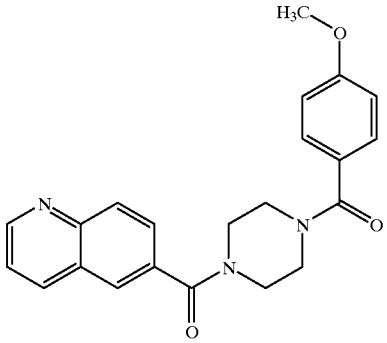 |
| 101 | 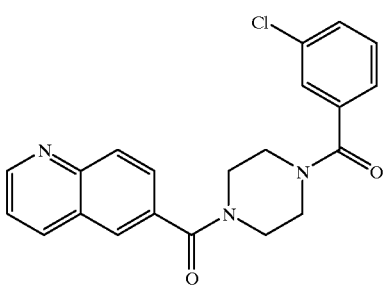 |
| 102 | 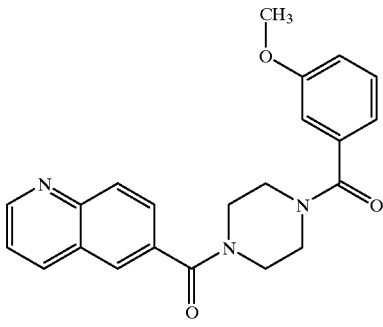 |
| 103 | 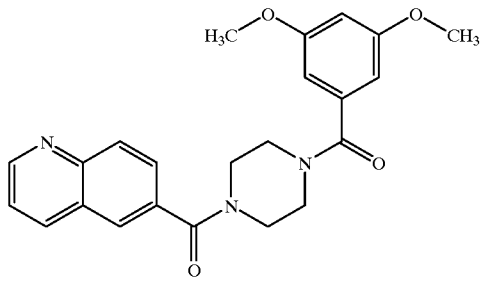 |
| 104 | 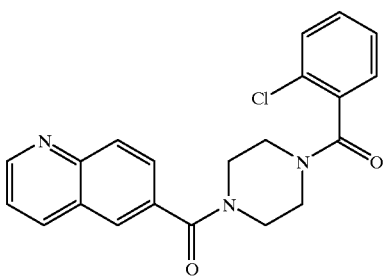 |

-continued
| Compound # | Structure |
|---|---|
| 105 | 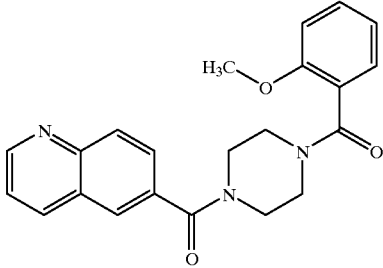 |
| 106 | 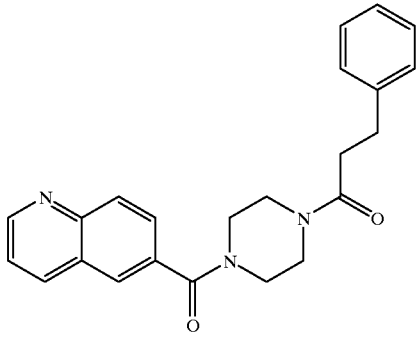 |
| 107 | 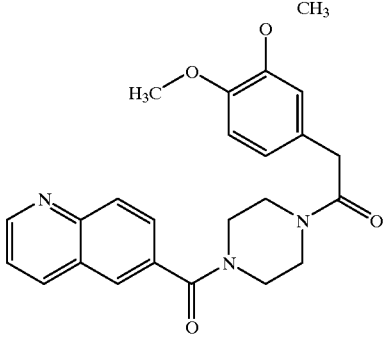 |
| 108 | 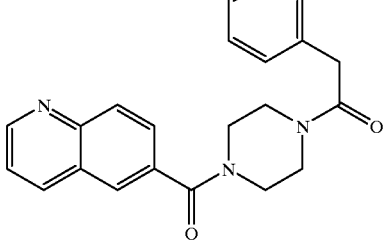 |

-continued
| Compound # | Structure |
|---|---|
| 109 | 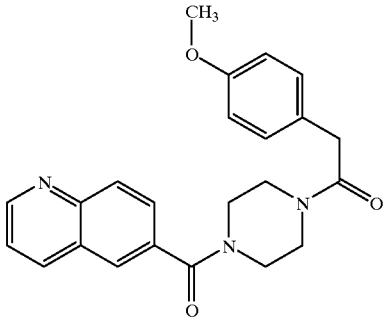 |
| 110 | 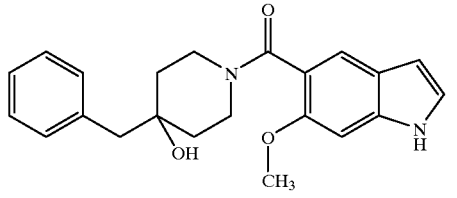 |
| 111 | 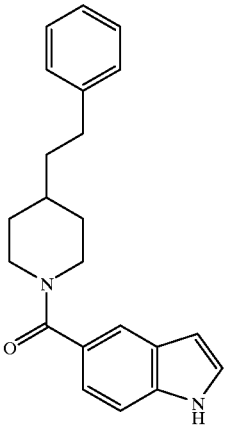 |
| 112 | 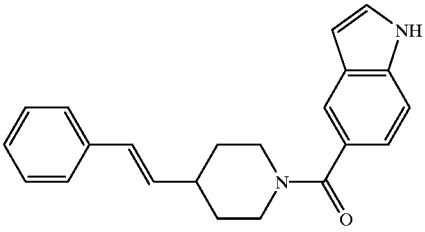 |

The invention is also directed to methods to prepare the compounds useful in the invention by forming the carboxamides from the appropriate aroyl compounds as halides or free acids.

Synthesis Methods

Preferably, the compounds useful in the invention are synthesized, generally, by coupling an aroyl moiety to a benzyl-substituted piperazine or piperidine. The general approach is shown in Reaction Schemes 1–6 hereinbelow. Reaction Scheme 3 is directed to the particular circumstance wherein Ar² includes an amino group to be functionalized in the presence of potentially competing groups.

Reaction Scheme 1

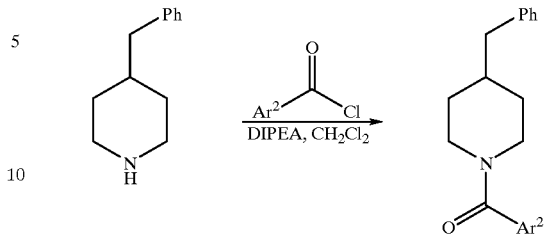

Reaction Scheme 2

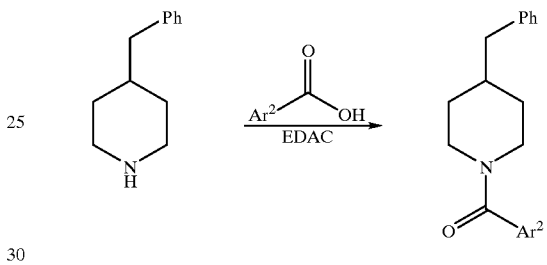

Reaction Scheme 3

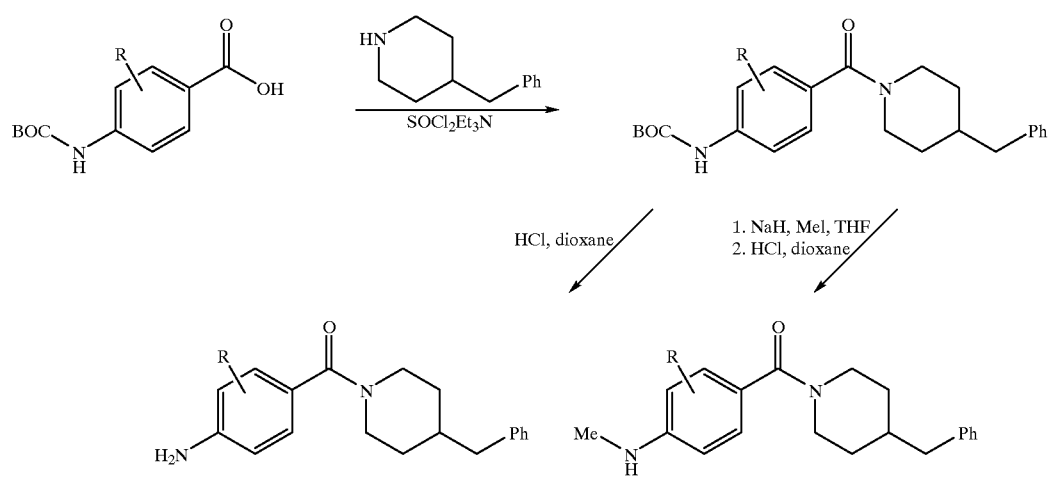

Reaction Scheme 4

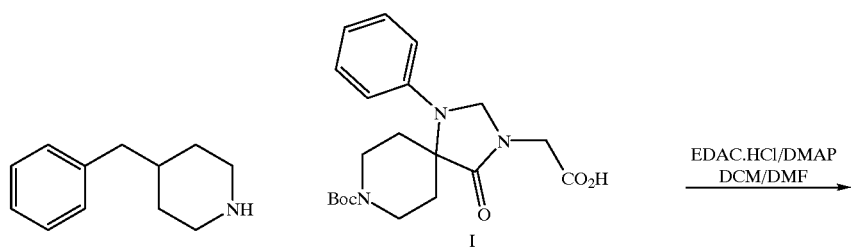

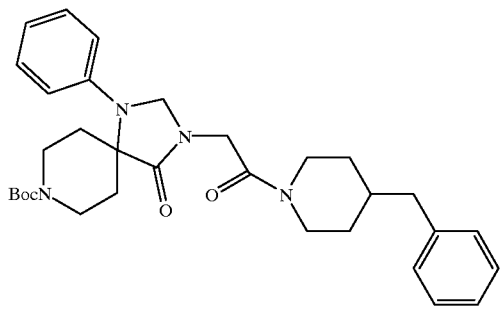
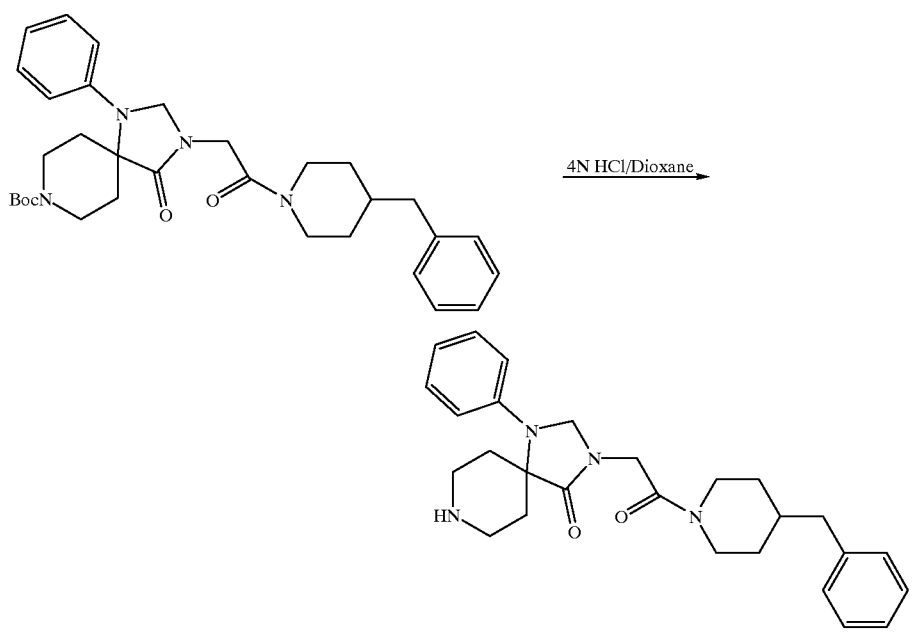
Reaction Scheme 5
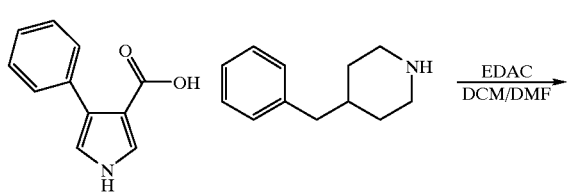
Reaction Scheme 6
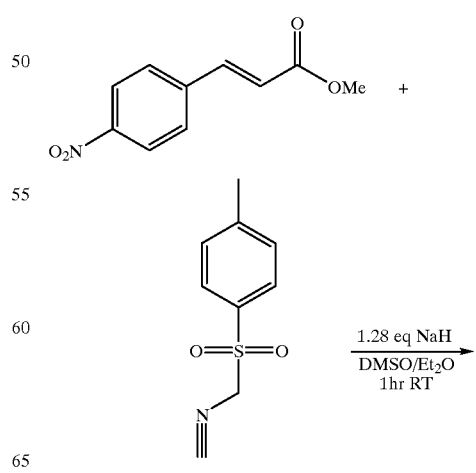

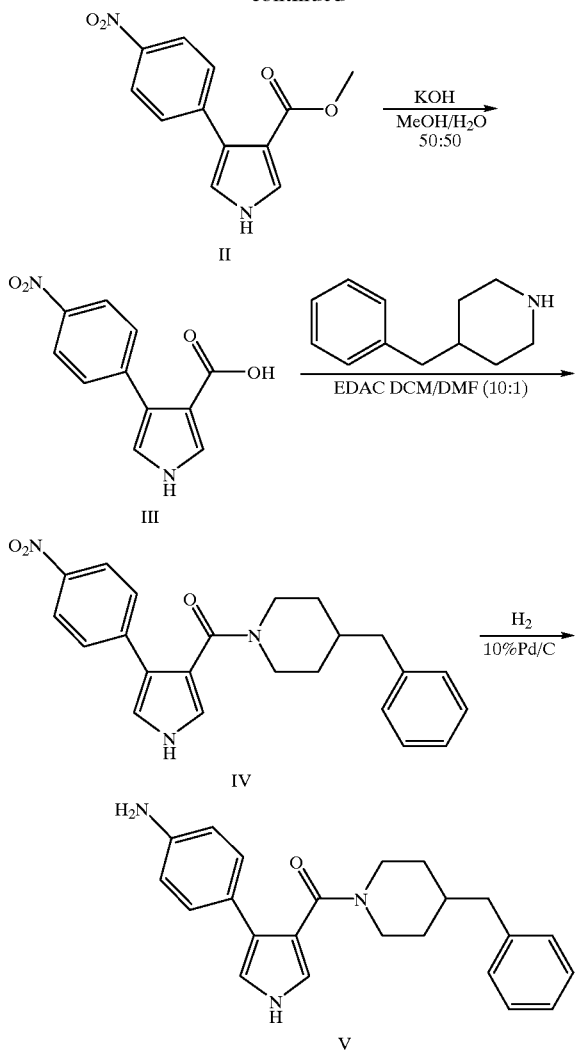

Administration and Use

The methods of the invention are directed to treating conditions associated with p38 kinase activity, for example, inflammatory conditions. Thus, the compounds of formula (1) or their pharmaceutically acceptable salts are used in the manufacture of a medicament for prophylactic or therapeutic treatment of mammals, including humans, in respect of conditions characterized by excessive production of cytokines and/or inappropriate or unregulated cytokine activity on such cells as cardiomyocytes, cardiofibroblasts and macrophages.

The compounds of formulas (1) and (2) inhibit the production of cytokines such as TNF, IL-1, IL-6 and IL-8, cytokines that are important proinflammatory constituents in many different disease states and syndromes. Thus, inhibition of these cytokines has benefit in controlling and mitigating many diseases. The compounds of formulas (1) and (2) are shown herein to inhibit a member of the MAP kinase family variously called p38 MAPK (or p38), CSBP, or SAPK-2. The activation of this protein has been shown to accompany exacerbation of the diseases in response to stress caused, for example, by treatment with lipopolysaccharides or cytokines such as TNF and IL-1. Inhibition of p38 activity, therefore, is predictive of the ability of a medicament to provide a beneficial effect in treating diseases such as coronary artery disease, congestive heart failure, cardiomyopathy, myocarditis, vasculitis, restenosis, such as occurs following coronary angioplasty, atherosclerosis, rheumatoid arthritis, rheumatoid spondylitis, osteoarthritis, gouty arthritis and other arthritic conditions, multiple sclerosis, acute respiratory distress syndrome (ARDS), asthma, chronic obstructive pulmonary disease (COPD), silicosis, pulmonary sarcosis, sepsis, septic shock, endotoxic shock, toxic shock syndrome, heart and brain failure (stroke) that are characterized by ischemia and reperfusion injury, surgical procedures, such as transplantation procedures and graft rejections, cardiopulmonary bypass, coronary artery bypass graft, CNS injuries, including open and closed head trauma, inflammatory eye conditions such as conjunctivitis and uveitis, acute renal failure, glomerulonephritis, inflammatory bowel diseases, such as Crohn's disease or ulcerative colitis, graft vs host disease, bone resorption diseases like osteoporosis, type II diabetes, pyresis, psoriasis, cachexia, viral diseases such as those caused by HIV, CMV, and Herpes, and cerebral malaria.

Within the last several years, p38 has been shown to comprise a group of MAP kinases designated p38α, p38β, p38γ and p38δ. Jiang, Y. et al. *J Biol Chem* (1996) 271:17920–17926 first reported characterization of p38β, as a 372-amino acid protein closely related to p38α. Kumar, S. et al. *Biochem Biophys Res Comm* (1997) 235:533–538 and Stein, B. et al. *J Biol Chem* (1997) 272:19509–19517 reported a second isoform of p38β, p38β2 containing 364 amino acids with 73% identity to p38α. All of these reports show evidence that p38β is activated by proinflammatory cytokines and environmental stress, although the second reported p38β isoform, p38β2, appears to be preferentially expressed in the CNS, heart and skeletal muscle compared to the more ubiquitous tissue expression of p38α. Furthermore, activated transcription factor-2 (ATF-2) was observed to be a better substrate for p38β2 than for p38α, thus suggesting that separate mechanisms of action may be associated with these forms. The physiological role of p38β1 has been called into question by the latter two reports since it cannot be found in human tissue and does not exhibit appreciable kinase activity with the substrates of p38α.

The identification of p38γ was reported by Li, Z. et al. *Biochem Biophys Res Comm* (1996) 228:334–340 and of p38δ by Wang, X., et al., *J Biol Chem* (1997) 272:23668–23674 and by Kumar, S., et al., *Biochem Biophys Res Comm* (1997) 235:533–538. The data suggest that these two p38 isoforms (γ and δ) represent a unique subset of the MAPK family based on their tissue expression patterns, substrate utilization, response to direct and indirect stimuli, and susceptibility to kinase inhibitors.

Various results with regard to response to drugs targeting the p38 family as between p38α and either the putative p38β1 or p38β2 or both were reported by Jiang, Kumar, and Stein cited above as well as by Eyers, P. A. et al. *Chem and Biol* (1995) 5:321–328. An additional paper by Wang, Y. et al. *J Biol Chem* (1998) 273:2161–2168 suggests the significance of such differential effects. As pointed out by Wang, a number of stimuli, such as myocardial infarction, hypertension, valvular diseases, viral myocarditis, and dilated cardiomyopathy lead to an increase in cardiac workload and elevated mechanical stress on cardiomyocytes. These are said to lead to an adaptive hypertrophic response which, if not controlled, has decidedly negative consequences. Wang cites previous studies which have shown that in ischemia reperfusion treated hearts, p38 MAPK activities are elevated in association with hypertrophy and programmed cell death. Wang shows in the cited paper that activation of p38β activity results in hypertrophy, whereas activation of p38α activity leads to myocyte apoptosis. Thus, selective inhibition of p38α activity as compared to p38β activity will be of benefit in treating conditions associated with cardiac failure. These conditions include congestive heart failure, cardiomyopathy, myocarditis, vasculitis, vascular restenosis, valvular disease, conditions associated with cardiopulmonary bypass, coronary artery bypass, grafts and vascular grafts. Further, to the extent that the α-isoform is toxic in other muscle cell types, α-selective inhibitors would be useful for conditions associated with cachexia attributed to TNF or other conditions such as cancer, infection, or autoimmune disease.

Thus, the invention is directed to the use of the compounds of formulas (1) and (2) which selectively inhibit the activity of the p38α isoform for treating conditions associated with activation of $p^{38}α$, in particular those associated with cardiac hypertrophy, ischemia or other environmental stress such as oxidation injury, hyperosmolarity or other agents or factors that activate p38α kinase, or cardiac failure, for example, congestive heart failure, cardiomyopathy and myocarditis.

The manner of administration and formulation of the compounds useful in the invention will depend on the nature of the condition, the severity of the condition, the particular subject to be treated, and the judgement of the practitioner; formulation will depend on mode of administration. As the compounds of formulas (1) and (2) are small molecules, they are conveniently administered by oral administration by compounding them with suitable pharmaceutical excipients so as to provide tablets, capsules, syrups, and the like. Suitable formulations for oral administration may also include minor components such as buffers, flavoring agents and the like. Typically, the amount of active ingredient in the formulations will be in the range of 5%–95% of the total formulation, but wide variation is permitted depending on the carrier. Suitable carriers include sucrose, pectin, magnesium stearate, lactose, peanut oil, olive oil, water, and the like.

The compounds of formulas (1) and (2) may also be administered through suppositories or other transmucosal vehicles. Typically, such formulations will include excipients that facilitate the passage of the compound through the mucosa such as pharmaceutically acceptable detergents.

The compounds may also be administered topically, for topical conditions such as psoriasis, or in formulation intended to penetrate the skin. These include lotions, creams, ointments and the like which can be formulated by known methods.

The compounds may also be administered by injection, including intravenous, intramuscular, subcutaneous or intraperitoneal injection. Typical formulations for such use are liquid formulations in isotonic vehicles such as Hank's solution or Ringer's solution.

Alternative formulations include nasal sprays, liposomal formulations, slow-release formulations, and the like, as are known in the art.

Any suitable formulation may be used. A compendium of art-known formulations is found in *Remington's Pharmaceutical Sciences*, latest edition, Mack Publishing Company, Easton, Pa. Reference to this manual is routine in the art.

The dosages of the compounds of formula (1) will depend on a number of factors which will vary from patient to patient. However, it is believed that generally, the daily oral dosage will utilize 0.001–100 mg/kg total body weight, preferably from 0.01–50 mg/kg and more preferably about 0.01 mg/kg–10 mg/kg. The dose regimen will vary, however, depending on the conditions being treated and the judgment of the practitioner.

The inhibitors of p38 kinase can be used as single therapeutic agents or in combination with other therapeutic agents. Drugs that could be usefully combined with these compounds include natural or synthetic corticosteroids, particularly prednisone and its derivatives, monoclonal antibodies targeting cells of the immune system, antibodies or soluble receptors or receptor fusion proteins targeting immune or non-immune cytokines, and small molecule inhibitors of cell division, protein synthesis, or mRNA transcription or translation, or inhibitors of immune cell differentiation or activation.

As implicated above, although the compounds of formula (1) may be used in humans, they are also available for veterinary use in treating animal subjects.

The following examples are intended to illustrate but not to limit the invention.

EXAMPLE 1

Preparation of 4-benzylpiperidin-1-yl benzene carboxamide (1-benzoyl-4-benzyl piperidine)

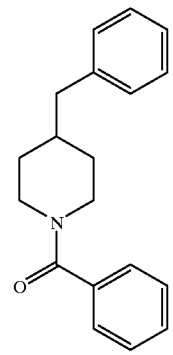

This example illustrates Reaction Scheme 1.

To a mixture of 4-benzylpiperidine (0.263 g, 1.5 mM) and diisopropylethyl-amine (0.53 mL, 3.0 mM) in 10 mL dichloromethane at room temperature was added benzoyl chloride (0.281 g, 2.0 mM) and the reaction mixture was stirred at room temperature for 20 h. The reaction mixture was poured into water and extracted with ethyl acetate (2×25 mL). The combined organic extract was washed with 1 N HCl, water and brine. The extract was dried over $Na_2SO_4$ and evaporated. The residue was chromatographed on a column of silica gel with ethyl acetate-hexane (10 to 50%, gradient). Evaporation of the desired fractions gave 0.402 g (96%) of the title compound as an oil. $^1$H NMR (CDCl$_3$): δ 7.10–7.40 (m, 10H), 4.60–4.70 (m, 1H), 3.70–3.80 (m, 1H), 2.80–2.90 (m, 1H), 2.70–2.80 (m, 1H), 2.60 (d, 2H), 1.70–1.80 (m, 1H), 1.50–1.70 (m, 2H), 1.20–1.40 (m, 2H). MS (ESI) m/e 279 (M$^+$).

EXAMPLE 2

Preparation of 4-Benzylpiperidin-1-yl-(4-amino) benzene carboxamide (1-(4-aminobenzoyl)-4-benzyl piperidine)

This example illustrates Reaction Scheme 2:

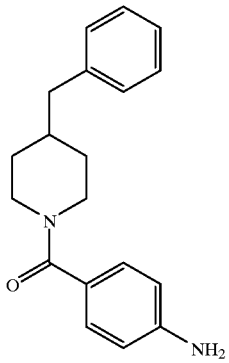

4-Aminobenzoic acid (1.61 g, 10 mM) was reacted with EDAC (1.92 g, 10 mM) in 40 mL dry DMF for 15 minutes. 4-Benzylpiperidine (1.75 g, 10 mM) was added followed by DMAP (20 mg, catalyst ) and the reaction mixture was stirred for 20 h. The mixture was poured into water and extracted with methylene chloride (3×100 mL). The combined extract was washed with dilute hydrochloric acid, saturated sodium bicarbonate and water and dried over $MgSO_4$. After evaporation of the solvent, the residue was chromatographed with methylene chloride-methanol (0 to 2% methanol, gradient) to yield 1.60 g (50%) of the title compound after recrystallization from ether-Hexane. $^1$H NMR (CDCl$_3$): δ 7.40–7.10 (m, 7 H), 6.70 (d, 2 H), 3.95–3.90 (broad m, 2 H), 2.85–2.75 (broad m, 2 H), 2.6 (d, 2 H), 1.85–1.80 (m, 1 H), 2.75–2.65 (broad m, 2 H), 1.15–1.05 (broad m, 2 H). MS (ESI) m/e 294 (M$^+$).

Examples 3 and 4 illustrate Reaction Scheme 3:

EXAMPLE 3

Preparation of 1-(2-chloro-4-aminobenzoyl)-4-benzyl piperidine

A. Preparation of the BOC-protected Intermediate

To a solution of 2-Chloro-4-t-butoxycarbonylaminobenzoic acid (0.50 g, 1.85 mM) in CH$_2$Cl$_2$ (8.0 mL) was added triethylamine (0.37 g, 0.52 mL, 3.70 mM) and 4-benzylpiperidine (0.65 g, 0.65 mL, 3.70 mM). This was followed by the dropwise addition of thionyl chloride (0.44 g, 0.27 mL, 3.70 mM). The mixture was allowed to stir at room temperature for 1 h, whereupon it was poured into water and extracted with CH$_2$Cl$_2$ (3×10 mL). The combined organics were dried over Na$_2$SO$_4$ and evaporated. Silica gel chromatography (5% methanol in dichloromethane) afforded 0.30 g (38%) of BOC-protected intermediate, i.e., 1-(2-chloro-4-t-butoxycarbonyl aminobenzoyl)-4-benzyl piperidine. $^1$H NMR (CDCl$_3$): δ 7.30–7.10 (m, 2 H), 6.60 (s, 1 H), 4.70 (m, 1 H), 3.30 (m, 1 H), 2.50 (d, 2 H), 1.80 (m, 2 H), 1.60 (m, 2 H), 1.50 (s, 9 H), 1.20 (m, 3 H). MS (ESI) m/e 428 (M$^+$).

B. 1-(2-chloro-4-t-butoxycarbonyl aminobenzoyl)-4-benzyl piperidine (0.15 g, 0.35 mM) from paragraph A was added to 4.0 N HCl in dioxane (2.0 mL). The mixture was stirred for 2 hours at room temperature whereupon it was triturated with Et$_2$O. The Et$_2$O was decanted and the residue was dried in vacuo to yield 0.10 g (87%) of the title compound. $^1$H NMR (CDCl$_3$): δ 7.50 (m, 3 H), 7.30 (m, 4 H), 7.20 (d, 1 H), 7.10 (d, 2 H), 4.6 (t, 1 H) 3.30 (d, 1 H), 2.90 (t, 1 H), 2.70 (t, 1 H), 2.50 (s, 2 H), 1.70 (d, 2 H), 1.60 (t, 1 H), 1.20 (broad s, 2 H). MS (ESI) m/e 327 (M$^+$–1).

EXAMPLE 4

Preparation of 1-(2-chloro-4-methylaminobenzoyl)-4-benzyl piperidine

A solution of 1-(2-chloro-4-t-butoxycarbonyl aminobenzoyl)-4-benzyl piperidine (0.88 g, 2.06 mM) in THF (4.0 mL) from paragraph A of Example 3 was added dropwise to an ice-cooled suspension of NaH in THF (4.0 mL). Stirring was continued for 0.5 hours before adding iodomethane (0.35 g, 0.15 mL, 2.47 mM) dropwise. The mixture was then allowed to stir at room temperature for 16 hours, at which time it was poured into water and extracted with ethyl acetate (3×10 mL). The combined extracts were dried over Na$_2$SO$_4$ and concentrated. The residue was dissolved in 4.0 N HCl in dioxane (10.0 mL) and stirred at room temperature for 2 hours whereupon it was triturated with Et$_2$O. The Et$_2$O was decanted and the residue was dried in vacuo to yield 0.56 g (79%) of 1-(2-chloro-4-methylaminobenzoyl)-4-benzyl piperidine. $^1$H NMR (CDCl$_3$): δ 7.60–7.10 (m, 8 H), 4.70 (t, 1 H), 3.40 (broad s, 1 H), 3.00 (m, 1 H), 2.90 (s, 3 H), 2.70 (m, 1 H) 2.60 (m, 1 H), 1.80 (broad s, 2 H), 1.60 (broad s, 1 H), 1.30 (m, 2 H). MS (ESI) m/e 342 (M$^+$).

EXAMPLE 5

Preparation of Additional Compounds of Formula (2)

Using the techniques set forth in Examples 1–4, the following additional compounds of the invention were prepared:

1-(4-methoxybenzoyl)-4-benzyl piperidine,
1-(4-cyanobenzoyl)-4-benzyl piperidine,
1-(4-phenylbenzoyl)-4-benzyl piperidine,
1-(3-methoxybenzoyl)-4-benzyl piperidine,
1-(3,5-dimethoxybenzoyl)-4-benzyl piperidine,
1-(2-chlorobenzoyl)-4-benzyl piperidine,
1-(2-bromobenzoyl)-4-benzyl piperidine,
1-(2-iodobenzoyl)-4-benzyl piperidine,
1-(2-methoxybenzoyl)-4-benzyl piperidine,
1-(2-methylbenzoyl)-4-benzyl piperidine,
1-(2-phenylbenzoyl)-4-benzyl piperidine,
1-(2-(2-carbomethoxyethen-1-yl)benzoyl)-4-benzyl piperidine,
1-(2-naphthoyl)-4-benzyl piperidine,
1-(1-naphthoyl)-4-benzyl piperidine,
1-(2-furanoyl)-4-benzyl piperidine,
1-(2-thiophenoyl)-4-benzyl piperidine,
1-(2-dimethylaminobenzoyl)-4-benzyl piperidine,
1-(3-dimethylaminobenzoyl)-4-benzyl piperidine,
1-(4-dimethylaminobenzoyl)-4-benzyl piperidine,
1-(3,4,5-trimethoxybenzoyl)-4-benzyl piperidine,
1-(2-acetamidobenzoyl)-4-benzyl piperidine, 1-(3-acetamidobenzoyl)-4-benzyl piperidine,
1-(4-acetamidobenzoyl)-4-benzyl piperidine, and
1-(4-formamidobenzoyl)-4-benzyl piperidine.

EXAMPLE 6

Preparation of 1-Phenyl-8-1,3,8-triazaspiro[4.5]
decan-4-one-3-acetyl-4-benzylpiperidine This example illustrates Reaction Scheme 4.

Acid I [*J Med Chem* (1996), 39(16):3169–3173]: 1.0 g, 2.57 mmol and 4-Benzylpiperidine, (0.46 g, 2.6 mmol) were treated with 0.51 g EDAC.HCl in 10 mL dichloromethane (DCM) in the presence of 200 µL 0.1M DMAP in DMF. After stirring at room temperature for 4 hours, the reaction mixture was concentrated and the residue was taken up in 50 mL ethyl acetate (EtOAc). The EtOAc layer was washed with 10% aqueous sodium carbonate, 10% aqueous hydrochloric acid, sodium chloride solution and dried over anhydrous sodium sulfate. Concentration gave crude product as a white solid. This material was chromatographed using ethylacetate/hexane on silica gel to the give Boc-protected compound as a white solid. 700 mg EIMS $M^+$ 546. 100 mg of the Boc-protected compound was treated with 10 mL 4N HCl in dioxane for 60 mins. The reaction mixture was concentrated and the solid obtained was filtered through a sintered glass funnel and washed with hexane. Extensive drying gave the hydrochloride salt of Example 1. EIMS $M^+$ 446. 65 mg.

EXAMPLE 7

Preparation of 4-Phenyl-3-pyrroyl-4-benzylpiperidine

This example illustrates Reaction Scheme 4.

4-Phenyl-3-pyrrole carboxylic acid (333 mg, 3 mole) and 4-Benzylpiperidine (525 mg 3 mmole) were dissolved in 15 ml dichloromethane/dimethylformamide(1.1). EDAC-HCl (573 mg, 3 mmole) was added and the reaction mixture was stirred overnight. The solvent was removed and residue redissolved in EtOAc, the EtOAc was washed with 10% HCl, 0.1M NaOH, water, the EtOAc extract was dried over magnesium sulfate (anh). Evaporated EtOAc to obtain 489 mg product.

Unless otherwise indicated all compounds were prepared following the method outlined above using carboxylic acids that are either commercially available or are available by synthesis, using methods known in the literature.

EXAMPLE 8

Preparation of (V) 4-(4')-Nitrophenyl-3-purroyl-4-benzylpiperidine

This example illustrates Reaction Scheme 6.

Preparation of II: Sodium hydride (614 mg 25.6 mmole) was suspended in 40 ml diethyl ether. Methyl 4-nitrophenyl-trans-cinnamate (4.14 g, 20 mmole), tosylmethylisocyanate (4.29 g, 22 mole) dissolved in Et2O/DMSO (2:1) 40 ml were added dropwise under nitrogen over 20 min period. The mixture was stirred for 1 hour at room temperature. Water was added to the reaction mixture and precipitate was filtered. The aqueous layer was extracted with Et2O (2×75 ml), The combined extracts were dried over MgSO4 and solvent removed under reduced pressure to give 1.42 g product. EIMS $M^+$ 247.

Preparation of III: Methyl-3-(4-nitrophenyl)-2-pyrrole carboxylate (626 mg 2.54 mmole) was treated with potassium hydroxide (713 mg, 12.7 mmole) in methanol/water (50:50). The reaction mixture was refluxed 2.5 hours. Methanol was evaporated, the solution was cooled and acidified with HCl(aq) to pH 7. The mixture was extracted with ethyl acetate, combined extracts dried over MgSO4 (anh.) and concentrated to give 440 mg product. EIMS $M^+$ 232.

Preparation of IV: 3-(4-nitrophenyl)-2-pyrrole carboxylic acid (440 mg 1.89 mmole) and 4-Benzylpiperidine (331 mg 1.89 mmole) were dissolved in DCM/DMF(10:1), EDAC (360 mg, 1.89 mmole) was added and the reaction mixture was stirred for 18 hr at room temperature. The solvent was evaporated, residue dissolved in EtOAc, washed with 10% HCl, 0.10M NaOH, water, the EtOAc layer was dried over $MgSO_4$, solvent evaporated to give 240 mg product. Product was chromatographed on silica gel with EtOAc:hex (8:2) to give 180 mg purified product. EIMS $M^+$ 389.

Preparation of (V) 4-(4')-Nitrophenyl-3-purroyl-4-benzylpiperidine: 180 mg of the nitro compound was dissolved in 10 ml methanol, 10% Pd/C (60 mg) was added and hydrogenated under hydrogen balloon for 2 hours. The catalyst was filtered over celite, solvent was evaporated to give 136 mg of the desired product. EIMS $M^+$ 359.

EXAMPLE 9

Assay for p38 Kinase Inhibition

The compounds to be tested were solubilized in DMSO and diluted into water to the desired concentrations. The p38 kinase was diluted to 10 µg/ml into a buffer containing 20 mM MOPS, pH 7.0, 25 mM beta-glycerol phosphate, 2 mg/ml gelatin, 0.5 mM EGTA, and 4 mM DTT.

The reaction was carried out by mixing 20 µl test compound with 10 µl of a substrate cocktail containing 500 µg/ml peptide substrate and 0.2 mM ATP (+200 µCi/ml gamma-32P-ATP) in a 4×assay buffer. The reaction was initiated by the addition of 10 µl of p38 kinase. Final assay conditions were 25 mM MOPS, pH 7.0, 26.25 mM beta-glycerol phosphate, 80 mM KCl, 22 mM $MgCl_2$, 3 mM $MgSO_4$, 1 mg/ml gelatin, 0.625 mM EGTA, 1 mM DTT, 125 µg/ml peptide substrate, 50 µM ATP, and 2.5 µg/ml enzyme. After a 40 minute incubation at room temperature, the reaction was stopped by the addition of 10 µl per reaction of 0.25 M phosphoric acid.

A portion of the reaction was spotted onto a disk of P81 phosphocellulose paper, the filters were dried for 2 minutes and then washed 4× in 75 mM $H_3PO_4$. The filters were rinsed briefly in 95% ethanol, dried, then placed in scintillation vials with liquid scintillation cocktail.

Alternatively, substrate is previously biotinylated and the resulting reactions are spotted on SAM²™ streptavidin filter squares (Promega). The filters are washed 4× in 2M NaCl, 4× in 2M NaCl with 1% phosphoric acid, 2× in water, and briefly in 95% ethanol. The filter squares are dried and placed in scintillation vials with liquid scintillation cocktail.

Counts incorporated are determined on a scintillation counter. Relative enzyme activity is calculated by subtracting background counts (counts measured in the absence of enzyme) from each result, and comparing the resulting counts to those obtained in the absence of inhibitor. $IC_{50}$ values were determined with curve-fitting plots available with common software packages. Approximate $IC_{50}$ values were calculated using formula $$IC_{50}(app)=A \times i/(1-A)$$

where A=activity and i=total inhibitor concentration.

The percent inhibition of p38-α kinase was determined at various concentrations in order to determine IC$_{50}$ values. Table 1 shows compounds tested for the percent inhibition of p38-α kinase at concentrations of 15 μM, 5 μM, 1 μM and 0.2 μM. The table shows various embodiments of Ar$^1$X$^1$; unless otherwise noted, Ph is unsubstituted phenyl, Z is CH and n is 0. Thus, all of the compounds in Table 1 are 4-benzyl piperidines, unless otherwise noted. All show substantial inhibition at 15 μM, some as high as 99%. Virtually all are inhibitory at 0.2 μM.

TABLE 1

| Comp. No. | Ar$^1$X$^1$ |
| --- | --- |
| 1 | benzoyl |
| 2 | 4-methoxybenzoyl |
| 3 | 4-cyanobenzoyl |
| 4 | 4-phenylbenzoyl |
| 5 | 3-methoxybenzoyl |
| 6 | 3,5-dimethoxybenzoyl |
| 7 | 2-chlorobenzoyl |
| 8 | 2-bromobenzoyl |
| 9 | 2-iodobenzoyl |
| 10 | 2-methoxybenzoyl |
| 11 | 2-methylbenzoyl |
| 12 | 2-(2-carbomethoxy ethen-1-yl) benzoyl |
| 13 | 2-naphthoyl |
| 14 | 1-naphthoyl |
| 15 | 2-furanoyl |
| 16 | 2-thiophenoyl |
| 17 | note 1 |
| 18 | 2-dimethylaminobenzoyl |
| 19 | 3-dimethylaminobenzoyl |
| 20 | 4-dimethylaminobenzoyl |
| 21 | 2-pyridoyl |
| 22 | 3-pyridoyl |
| 23 | 4-pyridoyl |
| 24 | note 2 |
| 25 | 3,4,5-trimethoxybenzoyl |
| 26 | 2-chloro-4-acetamidobenzoyl |
| 27 | 2-4-dimethylbenzoyl |
| 28 | 4-acetamidobenzoyl |
| 29 | 4-formamidobenzoyl |
| 30 | 2-aminobenzoyl |
| 31 | 3-aminobenzoyl |
| 32 | 4-aminobenzoyl |
| 33 | 4,5-dimethoxybenzoyl |
| 34 | 2,4-dimethoxybenzoyl |
| 35 | 2-hydroxybenzoyl |
| 36 | 2-benzoxybenzoyl |
| 37 | 3,5-bis-trifluoromethylbenzoyl |
| 38 | 2,6-dimethoxybenzoyl |
| 39 | 2-methylaminobenzoyl |
| 40 | 6-quinolyl |
| 41 | 2-chloro-4-benzamidoyl |
| 42 | 2-hydroxy-4-aminobenzoyl |
| 43 | 2-chloro-4-aminobenzoyl |
| 44 | 2-chloro-4-methylaminobenzoyl |
| 45 | 2-chloro-4-dimethylaminobenzoyl |
| 46 | 2-methoxy-4-nitrobenzoyl |
| 47 | 2-methoxy-4-aminobenzoyl |
| 48 | 4-guanidinobenzoyl |
| 49 | 2-bromobenzoyl (note 3) |
| 50 | phenylsulfonyl |
| 51 | 4-amino-3-pyridoyl |
| 52 | 2-methoxybenzoyl (note 4) |

Note 1: In compound 17, X$^1$ is CO and Ar$^1$ has the structure:

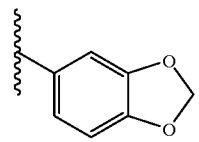

Note 2: In compound 24, X$^1$ is CO and Ar$^1$ has the structure:

TABLE 1-continued

| Comp. No. | Ar$^1$X$^1$ |
| --- | --- |

Note 3: In compound 49, n is 1 and Y is methyl. The methyl and benzyl group at the 4-position of the piperidine ring are cis to each other.

Note 4: In compound 52, Z is N; compound 52 is a piperazine derivative.

In some cases, IC$_{50}$ values have been determined as well as the ratio of IC$_{50}$ values for inhibition of β as compared to α p38 kinase. The compounds in Table 2 show IC$_{50}$ of about 200 nM to 1.5 μM. Those tested are specific for p38-α at least by a factor of 5.

TABLE 2

| Comp. No. | Ar$^1$X$^1$ |
| --- | --- |
| 1 | benzoyl |
| 2 | 4-methoxybenzoyl |
| 5 | 3-methoxybenzoyl |
| 7 | 2-chlorobenzoyl |
| 8 | 2-bromobenzoyl |
| 9 | 2-iodobenzoyl |
| 10 | 2-methoxybenzoyl |
| 11 | 2-methylbenzoyl |
| 16 | 2-thiophenoyl |
| 18 | 2-dimethylaminobenzoyl |
| 19 | 3-dimethylaminobenzoyl |
| 20 | 4-dimethylaminobenzoyl |
| 28 | 4-acetamidobenzoyl |
| 29 | 4-formamidobenzoyl |
| 32 | 4-aminobenzoyl |
| 34 | 2,4-dimethoxybenzoyl |
| 35 | 2-hydroxybenzoyl |
| 38 | 2,6-dimethoxybenzoyl |
| 39 | 2-methylaminobenzoyl |
| 43 | 2-chloro-4-aminobenzoyl |
| 44 | 2-chloro-4-methylaminobenzoyl |
| 45 | 2-chloro-4-dimethylaminobenzoyl |
| 49 | 2-bromobenzoyl (note 3) |

EXAMPLE 10

Preparation of Ortho-Substituted Aroyl Derivatives

The aroyl piperidines or piperazines of formula (2) can be provided with ortho-substituents via metallation as described by Beak, P. et al., *J Org Chem* (1982) 47:34–46; Bindal, R. D. et al., *J Org Chem* (1987) 52:3181–3185; Gshwend, H. et al., *Org Rxns* (1979) 26:1. The general procedure is shown as follows:

Reaction Scheme 7

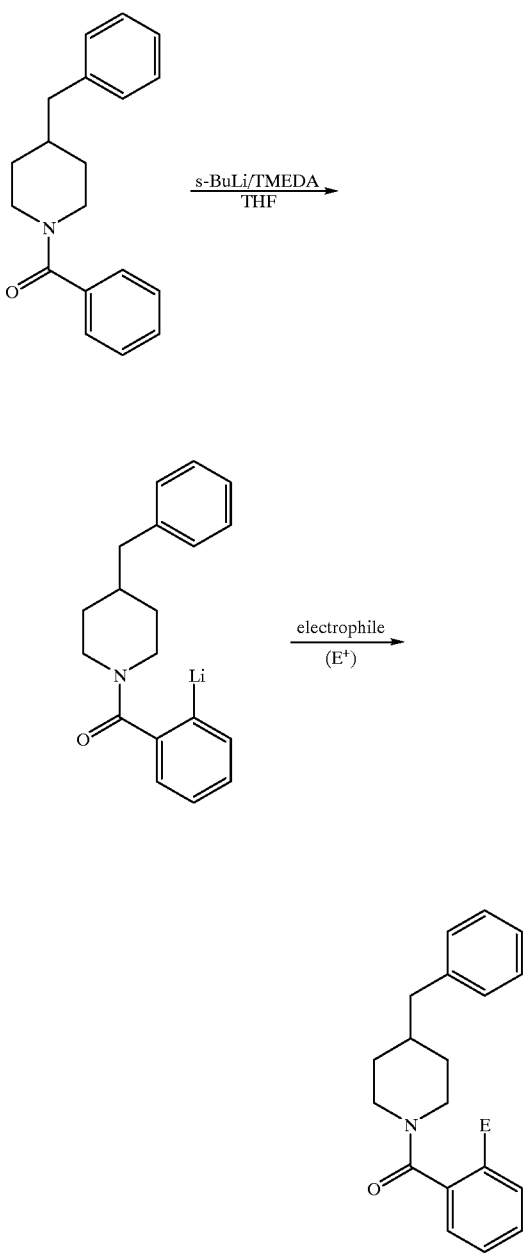

The starting material is first metallated with butyl lithium in the presence of base and then treated with an electrophile to provide the appropriate substitution. The electrophile may be an alkyl group, but additional functionality may be introduced by appropriate choice of the electrophile. For example, use of benzaldehyde as the source of the electrophile results in the secondary alcohol.

Compounds with further substitutions on the aroyl moiety can also be used as substrates, but those that contain an N—H require two equivalents of the butyl lithium/base.

EXAMPLE 11A

Preparation of 4-benzylpiperidin-1-yl-(2-methoxy-4-benzyloxy)benzene carboxamide

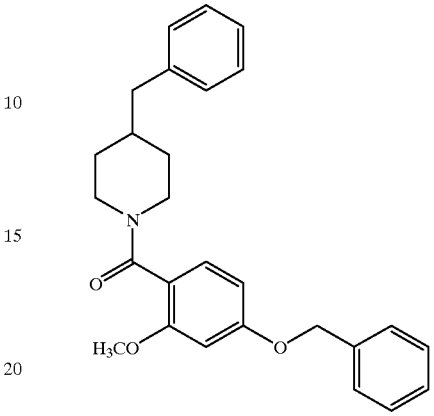

A. Methyl 2-hydroxy-4-benzyloxybenzoate: To a solution of methyl 2,4-dihydroxybenzoate (17.5 g, 104 mM) in acetone at 0° C. were added potassium carbonate (52.5 g, 350 mM) and benzyl bromide (13.8 mL, 116 mM). The mixture was stirred at 0° C. for 2 h, followed by stirring at RT for 16 h. This mixture was filtered through a pad of Celite and concentrated. The resulting material was partitioned between ethyl acetate and water. The organic layer was washed with a saturated sodium bicarbonate solution, dried ($Na_2SO_4$), filtered and concentrated. The residue was purified via silica gel chromatography with ethyl acetate-hexane (1 to 20%, gradient). Evaporation of the desired fractions resulted in 13.48 g (50%) of the title compound as a white solid. $^1$H-NMR (CDCl$_3$): δ 7.80 (d, 1 H), 7.50–7.30 (m, 5 H), 6.55 (m, 2 H), 5.10 (s, 2 H), 3.95 (s, 3 H). MS (ESI) m/e 258 (m$^+$).

B. Methyl 2-methoxy-4-benzyloxybenzoate: To an ice-cooled solution of methyl 2-hydroxy-4-benzyloxybenzoate from paragraph A (12.92 g, 50.1 mM) in DMF (200 mL) was added NaH in a 60% oil dispersion (3.00 g, 75.0 mM). The mixture was stirred for 5 min, at which time MeI (7.9 mL, 127 mM) was added dropwise. The mixture was allowed to stir at RT for 16 h, whereupon it was poured onto ice and extracted with ethyl acetate. The organics were washed with water and brine, then dried ($Na_2SO_4$) and concentrated to yield 13.11 g (96.3%) of the title compound as a tan solid. $^1$H-NMR (CDCl$_3$): δ 7.85 (d, 1 H), 7.50–7.30 (m, 5 H), 6.55 (m, 2 H), 5.15 (s, 2 H), 3.95 (s, 3 H), 3.90 (s, 3 H). MS (ESI) m/e 272 (m$^+$).

C. Title Compound: To a solution of 4-benzylpiperidine (27.5 mM, 4.85 mL) in toluene (75 mL) at −78° C. was added Me$_3$Al (2 M solution in hexane, 32.5 mM, 16.25 mL). The mixture was stirred at −78° C. for 10 min followed by stirring at RT for 1 h. The mixture was once again cooled to −78° C. and a solution of methyl 2-methoxy-4-benzyloxybenzoate from paragraph B (20.0 mM, 6.96 g) in toluene (25 mL) was added dropwise. Stirring was continued at −78° C. for 10 min, at which time the mixture was allowed to warm to RT and then refluxed for 16 h. The mixture was then cooled and quenched with water, made basic (pH 12) with 1 M NaOH, and stirred at RT for 0.5 h. The mixture was then extracted with ethyl acetate, washed with brine, dried (Na$_2$SO$_4$), filtered, and concentrated. The residue was purified via silica gel chromatography with ethyl acetate-hexane (10 to 60%). Evaporation of the desired fractions resulted in 639 mg (74.8%) of the title compound as an oil. $^1$H-NMR (CDCl$_3$): δ 7.60–7.10 (m, 11 H), 6.60 (m, 2 H), 5.10 (s, 2 H), 4.75 (br d, 1 H), 3.80 (app d, 3 H), 3.55 (br d, 1 H), 3.00–2.50 (m, 4 H), 1.80 (m, 2 H), 1.60 (m, 1H), 1.30 (m, 1 H), 1.10 (m, 1 H). MS (ESI) m/e 414 (m$^+$).

EXAMPLE 11B

Preparation of 4-benzylpiperidin-1-yl-(2-methoxy-4-hydroxy)benzene carboxamide

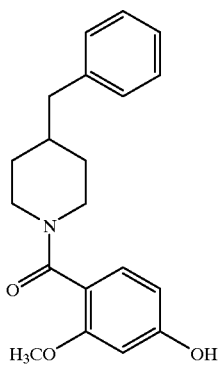

A Par hydrogenation vessel was charged with 4-benzylpiperidin- 1-yl-(2-methoxy-4-benzyloxy)benzene carboxamide from Example 11A (15.00 g, 36.14 mM), dissolved in MeOH (100 mL), and 5% palladium on carbon (1.2 g). The vessel was flushed, placed under 42 psi of H$_2$, and shaken for 16 h. The slurry was then filtered through Celite and concentrated. The crude material was recrystallized from ethyl acetate/hexane (1:10) to yield 11.24 g (95.7%) of the title compound as a white solid. $^1$H-NMR (CDCl$_3$): δ 7.40–6.80 (m, 6 H), 6.30 (m, 2 H), 4.75 (broad d, 2 H), 3.50 (app d, 3 H), 3.0–2.50 (m, 4 H), 1.75 (m, 2 H), 1.55 (m, 1 H), 1.20 (m, 1 H), 1.05 (m, 1 H). MS (ESI) m/e 324 (m$^+$).

EXAMPLE 12

Effect of Ortho-Substitution

Using the methods set forth in Example 10, 1-benzoyl-4-benzylpiperidine isomers, substituted on the benzoyl substituent at various positions, were tested for their ability to inhibit p38α kinase at 15 μM concentration. The results are shown in Table 3:

TABLE 3

| | % Inhibition of p38α kinase at 15 μM | | |
|---|---|---|---|
| | ortho | meta | para |
| F | 98 | 92 | 94 |
| Cl | 99 | 80 | 85 |
| Br | 99 | 74 | 96 |
| methyl | 98 | 90 | 97 |
| CF$_3$ | 98 | 49 | 66 |

As shown in Table 3, for any given substituent, the ortho isomer shows enhanced inhibition.

The IC$_{50}$ values, obtained as set forth in Example 10, were also determined for the ortho-, meta-, and para-methoxy substituted benzoyl forms of 1-benzoyl-4-benzylpiperidine. These results are shown in Table 4:

TABLE 4

| IC$_{50}$'s of methoxy analogs | |
|---|---|
| | IC$_{50}$ (μM) |
| ortho | 0.287 |
| meta | 1.1 |
| Para | 0.605 |

It is clear from these results that substitution at the ortho position is preferred.

The molar refraction values for the ortho derivatives containing chloro, bromo and methoxy substituents were determined as a measure of the size of the substituent as described by Hansch, C. et al., *J Med Chem* (1973) 16:1207–1216. A linear correlation between the MR values and percent inhibition of p38α at 200 nM concentrations of the compounds was obtained. The smallest substituent (chloro) showed an MR value of about 6 and 52% inhibition at 200 nM; the compound with an intermediate MR value of about 8 (methoxy) provided 68% inhibition at this concentration, and the compound having the largest substituent (bromo) showed an MR value of approximately 9 and 72% inhibition at this concentration. Thus, it appears that the ability to inhibit p38α kinase is dependent on the size of the ortho substituent. While not intending to be bound by any theory, applicants believe that the bulkier substituents rotate the aroyl moiety out of the plane of the piperidine or piperazine ring.

U.S. Provisional Applications Serial Nos. 60/098,219 and 60/125,343 are relied on and incorporated herein by reference in their entirety.

What is claimed is:

1. A method to treat a condition mediated by p38α kinase which method comprises administering to a subject in need of such treatment a compound of the formula:

(1)

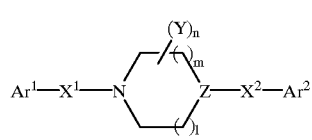

and the pharmaceutically acceptable salts thereof, or a pharmaceutical composition thereof, wherein Z is N or CR$^1$, wherein R$^1$ is selected from the group consisting of optionally substituted alkyl, alkoxy, aryl, arylalkyl, aryloxy, heteroaryl, amino, ureayl, carbamate, polyhaloalkoxy, halogen, acyl, carboxy, and hydroxy, each of X$^1$ and X$^2$ is a linker, wherein each said linker is independently saturated or unsaturated alkylene optionally containing 1–4 carbonyl, 1–4 SO$_2$, and/or 1–3 heteroatoms, including a linker which is itself CO, SO$_2$, SO or is itself a heteroatom, and said alkylene or suitable heteroatom optionally substituted with a substituent selected from the group consisting of halo, alkyl, alkoxy, cycloalkyl, aryl, aryloxy, arylalkyl, haloalkyl, polyhaloalkyl, haloalkoxy, polyhaloalkoxy, cycloheteroalkyl, cycloheteroalkylalkyl, heteroaryl, heteroarylalkyl, heteroaryloxy, arylthio, arylsulfinyl, arylsulfonyl, heteroarylthio, heteroarylsulfinyl, heteroarylsulfonyl, alkylaminocarbonyl, arylaminocarbonyl, heteroarylaminocarbonyl, alkoxycarbonyl, aryloxycarbonyl, heteroaryloxycarbonyl, acyl, aminocarbonyl, arylcarbonyl, heteroarylcarbonyl, cyano, carboxy, hydroxy, tetrazolyl, imidazole, oxazole, triazole, and —SOR wherein R is hydroxy, alkyl, aryl, alkoxy, aryloxy, cycloalkyl, heteroaryl, heteroarylalkyl, heteroaryloxy, heteroarylalkoxy and cycloheteroalkylalkoxy, $Ar^1$ and $Ar^2$ are identical or different, and represent optionally substituted aryl groups containing one or more rings optionally including one or more heteroatoms, selected from the group of O, N and S;

wherein $Ar^1$ and $Ar^2$ do not comprise an optionally substituted indolyl substituent; and with the proviso that when $X^2$ is $CH_2$ or an isostere thereof, $X^1$ is CO or an isostere thereof, and $Ar^2$ is optionally substituted phenyl, $Ar^1$ is other than benzimidazolyl or benzotriazolyl;

wherein Y is selected from the group consisting of optionally substituted alkyl, alkoxy, cycloalkyl, cycloheteroalkyl, aryl, cycloheteroalkyl, heteroaryl, halogen, alkylaminocarbonyl, arlyaminocarbonyl, heteroarylaminocarbonyl, acyl, carboxy, hydroxy, aminocarbonyl, arylcarbonyl, heteroarylcarbonyl, cyano, amino, and alkylamino, wherein n is an integer from 0–4, and wherein m is an integer from 0–4 and 1 is an integer from 0–3.

2. The method defined in claim 1, wherein when Z is N, $X^2$ is the same as $X^1$, or $X^2$ is —O—, —O[C(Rx)$_2$]$_r$— wherein Rx is optionally substituted alkyl, alkenyl or alkynyl and r is an integer from 1 to 4, —NR$^2$CO—, —SO$_2$NR$_2$—, —NR$^2$—, —S—, —SO—, SO$_2$, wherein $R^2$ is H, optionally substituted alkyl, cycloalkyl, aryl, arylalkyl, heteroaryl, heteroarylalkyl, carboxy, or acyl; or wherein when Z is $CR^1$, $X^2$ is $X^1$ or is —O[C(Rx)$_2$]$_r$ wherein Rx is —SO$_2$—.

3. The method defined in claim 1 wherein said alkylene group is C1–C4.

4. The method defined in claim 1, wherein said haloalkyl or polyhaloalkyl group as a substituent on said linker is $CF_3$ or $CF_3CH_2$; and wherein said haloalkoxy or polyhaloalkoxy group as a substituent on said linker is $CF_3O$ or $CF_3CH_2O$.

5. The method defined in claim 1, wherein at least one said aryl group has 6 to 12 carbon atoms and 0 to 3 heteroatoms.

6. The method defined in claim 5, wherein at least one said aryl group has 6 to 8 carbon atoms and 1 or 2 heteroatoms.

7. The method defined in claim 1, wherein at least one said aryl group is phenyl or residues of optionally benzo-fused heterocycles containing up to 3 heteroatoms selected from the group consisting of S, N and O.

8. The method defined in claim 1, wherein at least one said aryl group is a saturated or unsaturated 5- to 7-membered heterocycle.

9. The method defined in claim 8 wherein at least one said aryl group is a saturated or unsaturated 5- to 6-membered heterocycle.

10. The method defined in claim 1, wherein at least one said aryl group is selected from the group consisting of isoquinolyl, quinolyl, benzimidazolyl, benzotriazolyl, benzothiazolyl, benzofuranyl, pyridyl, thienyl, furyl, pyrrolyl, thiazolyl, oxazolyl, imidazolyl, morpholinyl and piperidyl.

11. A method to treat a condition mediated by p38α kinase which method comprises administering to a subject in need of such treatment a compound of the formula:

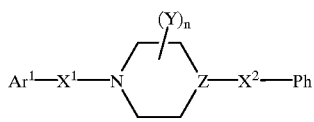

(2)

and the pharmaceutically acceptable salts thereof, or a pharmaceutical composition thereof, wherein $Ar^1$ is optionally substituted furanyl, thiophenyl, phenyl system containing 0, 1 or 2 N as heterocyclic atoms, or naphthyl system containing 0, 1, 2 or 3 N as heterocyclic atoms, $X^1$ is CO or an isostere thereof;

Y is optionally substituted alkyl (1–6C), optionally substituted aryl (6–10C), or optionally substituted arylalkyl (7–11C);

n is 0–1;

Z is N or CH;

$X^2$ is $CH_2$ or an isostere thereof; and

Ph is optionally substituted phenyl.

12. The method of claim 11 wherein Ph is unsubstituted, or wherein n is 0, or wherein Z is CH.

13. The method of claim 12 wherein n is 0 and Z is CH.

14. The method of claim 11 wherein $Ar^1$ is optionally substituted phenyl.

15. The method of claim 11 wherein $Ar^1X^1$ is benzoyl, 4-methoxybenzoyl, 4-cyanobenzoyl, 4-phenylbenzoyl, 3-methoxybenzoyl, 3,5-dimethoxybenzoyl, 2-chlorobenzoyl, 2-bromobenzoyl, 2-iodobenzoyl, 2-methoxybenzoyl, 2-methylbenzoyl, 2-(2-carbomethoxy ethen-1-yl) benzoyl, 2-naphthoyl, 1-naphthoyl, 2-furanoyl, 2-thiophenoyl, 2-dimethylaminobenzoyl, 3-dimethylaminobenzoyl, 4-dimethylaminobenzoyl, 2-pyridoyl, 3-pyridoyl, 4-pyridoyl, 3,4,5-trimethoxybenzoyl, 2-acetamidobenzoyl, 3-acetamidobenzoyl, 4-acetamidobenzoyl, 4-formamidobenzoyl, 2-aminobenzoyl, 3-aminobenzoyl, 4-aminobenzoyl, 4,5-dimethoxybenzoyl, 2,4-dimethoxybenzoyl, 2-hydroxybenzoyl, 2-benzoxybenzoyl, 3,5-bis-trifluoromethylbenzoyl, 2,6-dimethoxybenzoyl, 2-methylaminobenzoyl, 3-methylaminobenzoyl, 4-methylaminobenzoyl, 2-hydroxy-4-aminobenzoyl, 2-chloro-4-aminobenzoyl, 2-chloro-4-methylaminobenzoyl, 2-chloro-4-dimethylaminobenzoyl, 2-methoxy-4-nitrobenzoyl, 2-methoxy-4-aminobenzoyl, 4-guanidinobenzoyl, phenylsulfonyl, 4-amino-3-pyridoyl, 2-aminobenzoyl, 2-methoxy-4-hydroxybenzoyl, 2-methoxy-4-benzyloxybenzoyl, or 2-methoxy-4-methoxybenzoyl.

16. The method of claim 11 wherein formula (1) is 1-benzoyl-4-benzyl piperidine, 1-(3-methoxybenzoyl)-4-benzyl piperidine, 1-(4-phenylbenzoyl)-4-benzyl piperidine, 1-(2-chlorobenzoyl-4-benzyl piperidine, 1-(2- bromobenzoyl)-4-benzyl piperidine, 1-(2-iodobenzoyl)-4-benzyl piperidine, 1-(2-methoxybenzoyl)-4-benzyl piperidine, 1-(2-methylbenzoyl)-4-benzyl piperidine, 1-(2-naphthoyl)-4-benzyl piperidine, 1-(4-dimethylaminobenzoyl)-4-benzyl piperidine, 1-(4-acetamidobenzoyl)-4-benzyl piperidine, 1-(4-formamidobenzoyl)-4-benzyl piperidine, 1-(4-aminobenzoyl)-4-benzyl piperidine, 1-(2,4-dimethoxybenzoyl)-4-benzyl piperidine, 1-(2,6-dimethoxybenzoyl)-4-benzyl piperidine, 1-(2-chloro-4-aminobenzoyl)-4-benzyl piperidine, 1-(2-chloro-4-methylaminobenzoyl)-4-benzyl piperidine, 1-(2-chloro-4-dimethylaminobenzoyl)-4-benzyl piperidine, cis-1-(2-bromobenzoyl)-3-methyl-4-benzyl piperidine, 1-(2-methoxy-4-hydroxybenzoyl)-4-benzylpiperidine, 1-(2-methoxy-4-methoxybenzoyl)-4-benzylpiperidine, 1-(2-methoxy-4-benzyloxybenzoyl)-4-benzylpiperidine, or 1-(2-methoxy-4-methoxybenzoyl)-4-(4-fluorobenzyl)piperidine.

17. The method of claim 11 wherein said condition is characterized by a proinflammation response.

18. The method of claim 17 wherein said condition characterized by inflammation is acute respiratory distress syndrome, asthma, chronic obstructive pulmonary disease, uveitis, acute renal failure, head trauma, ischemic/reperfusion injury, multiple sclerosis, IBD, rheumatoid arthritis, rheumatoid spondylitis, osteoarthritis, gouty arthritis, other arthritic conditions, sepsis, septic shock, endotoxic shock, Gram-negative sepsis, toxic shock syndrome, adult respiratory distress syndrome, stroke, reperfusion injury, CNS injury, psoriasis, restenosis, cerebral malaria, chronic pulmonary inflammatory disease, silicosis, pulmonary sarcosis, a bone resorption disease, graft-versus-host reaction, Crohn's Disease, ulcerative colitis, or pyresis.

19. The method of claim 11 wherein said condition is a heart condition associated with cardiac failure.

20. The method of claim 19 wherein said chronic heart condition is congestive heart failure, cardiomyopathy or myocarditis.

21. The method defined in claim 1 further comprising administering said compound and an additional therapeutic agent.

22. The method defined in claim 1 wherein the compound is at least one compound selected from the group consisting of:

1)

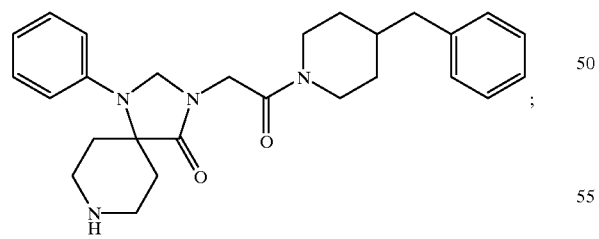

2)

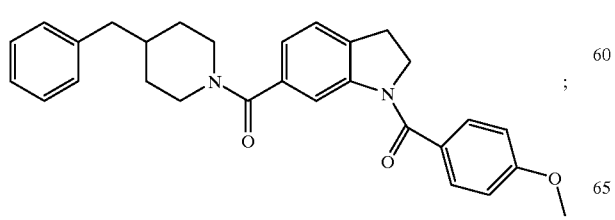

3)

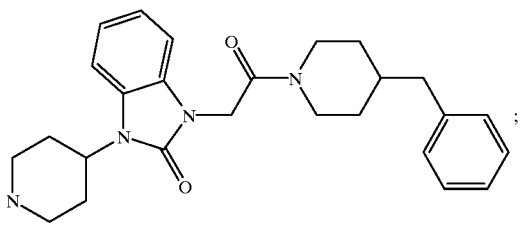

4)

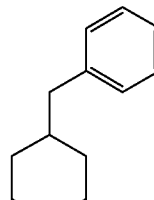

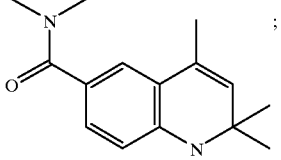

5)

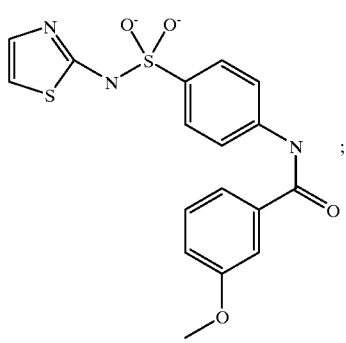

6)

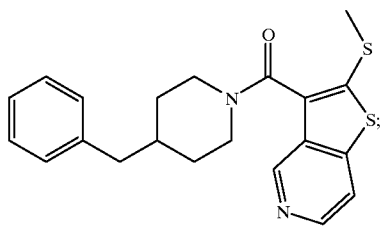

7)

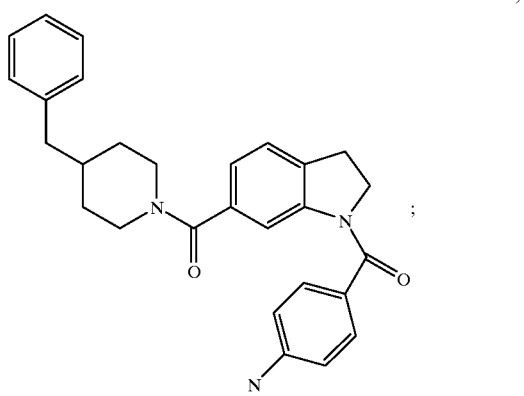

8)
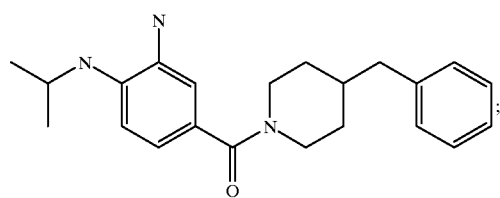
9)
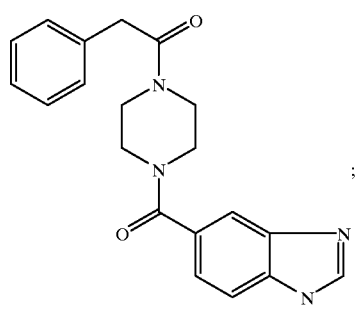
10)
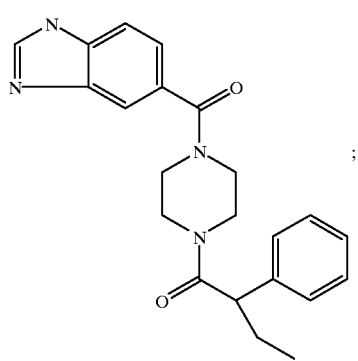
11)
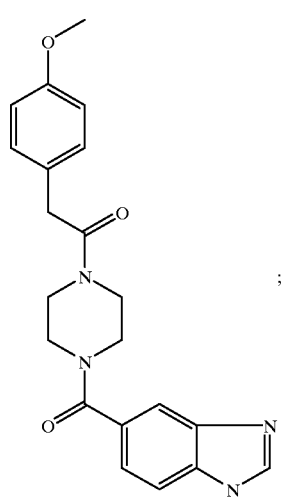
12)
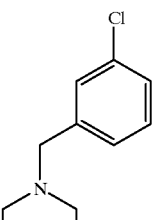
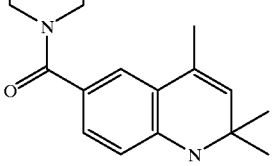
13)
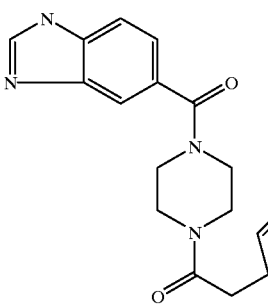
14)
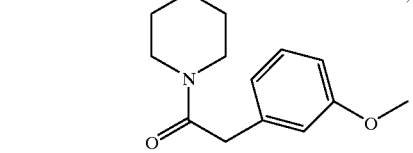
15)
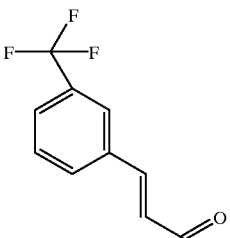

16)
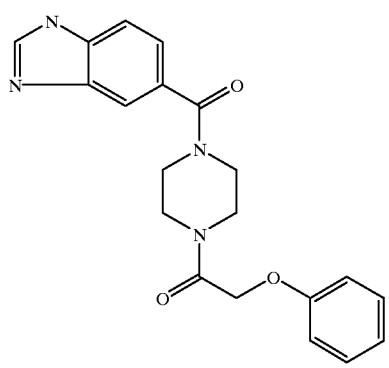
21)
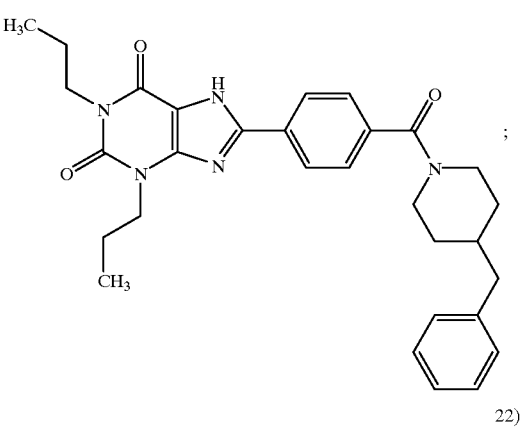
17)
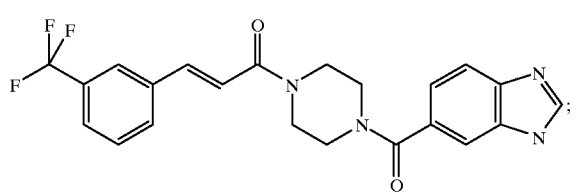
22)
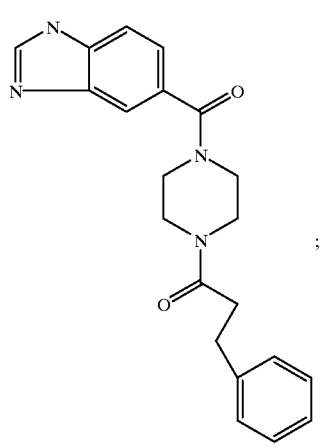
18)
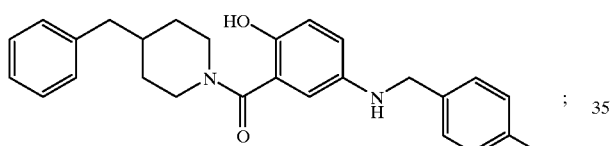
19)
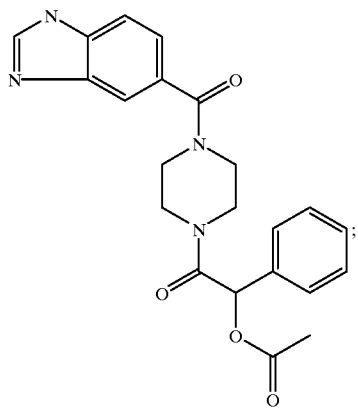
23)
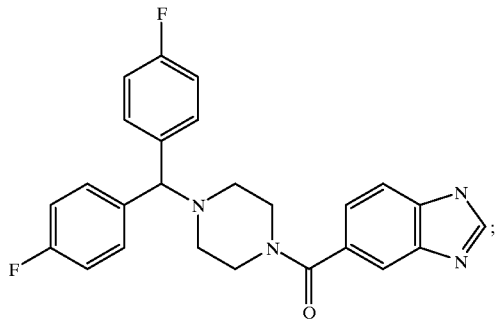
24)
20)
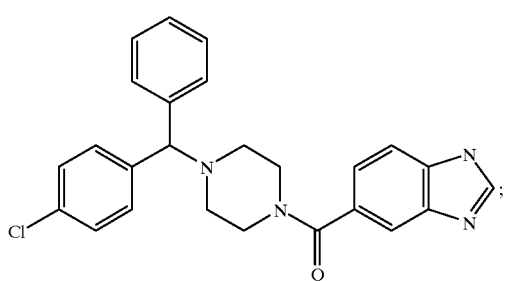
25)
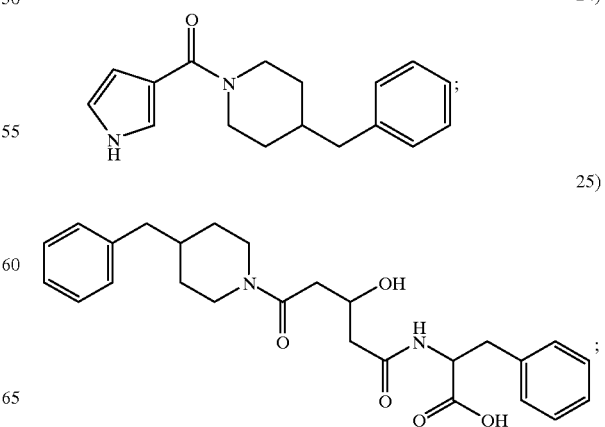

26) 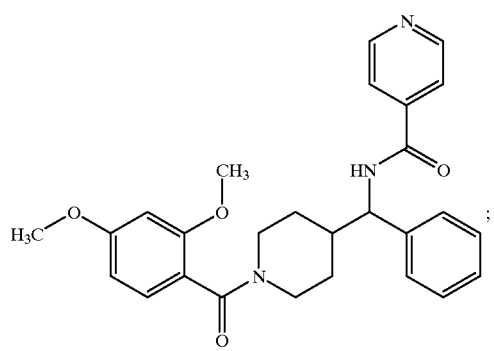
27) 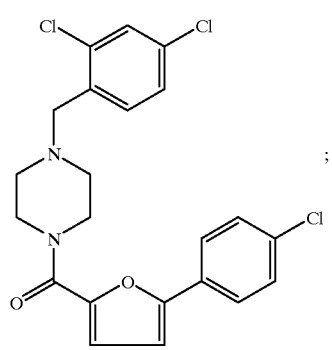
28) 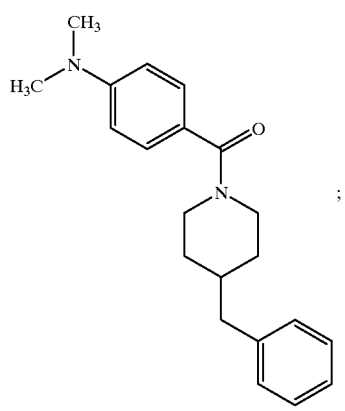
29) 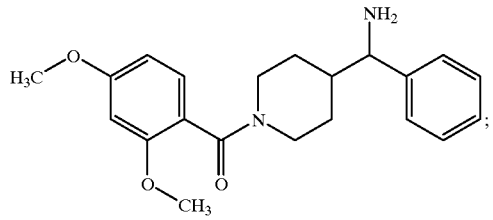
30) 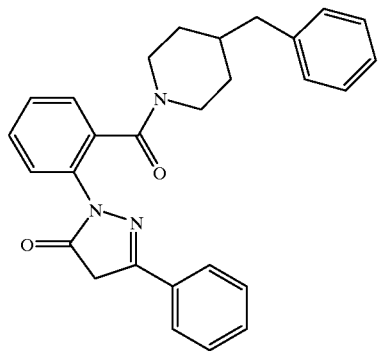
31) 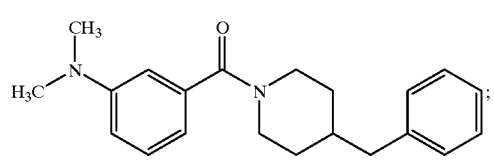
32) 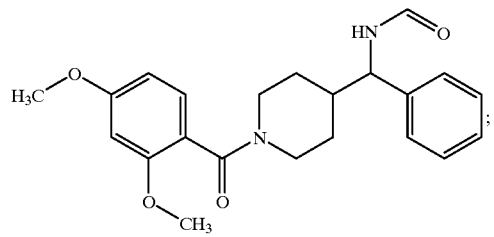
33) 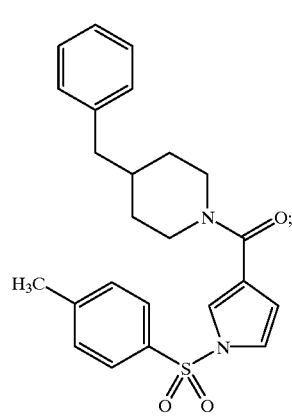
34) 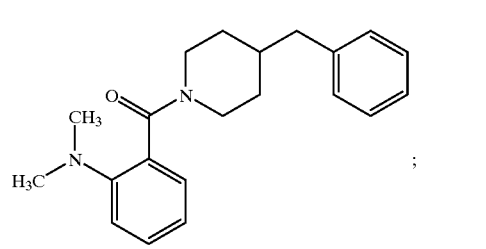

35)
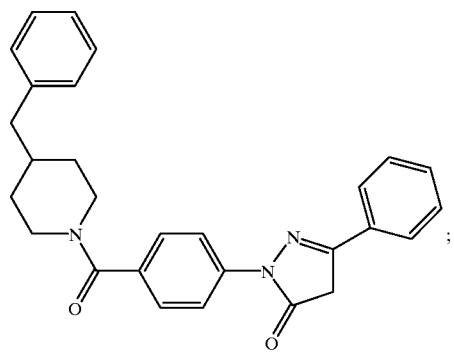
36)
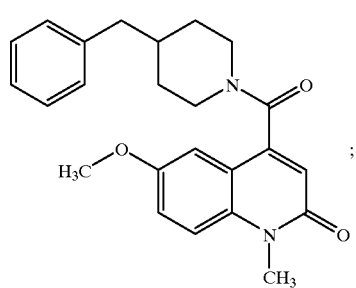
37)
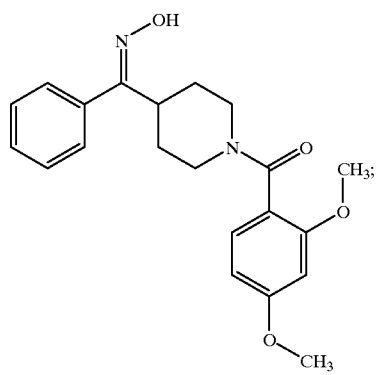
38)
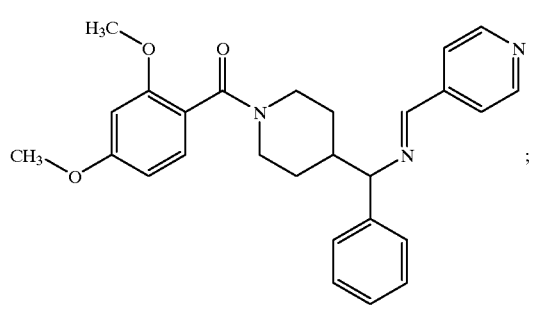
39)
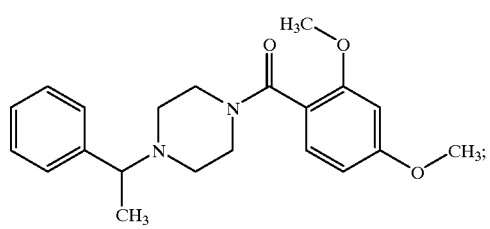
40)
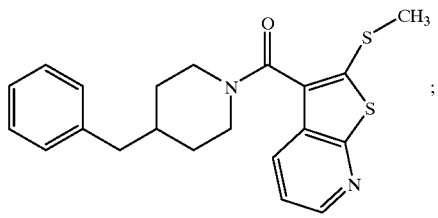
41)
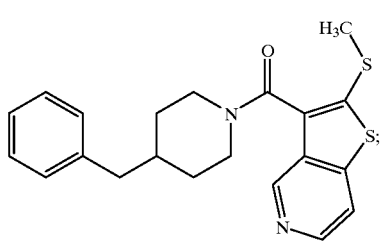
42)
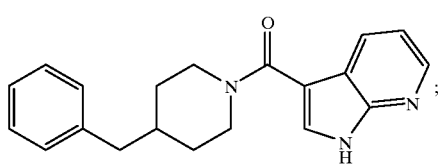
43)
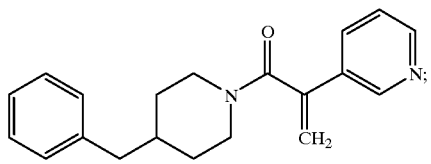
44)
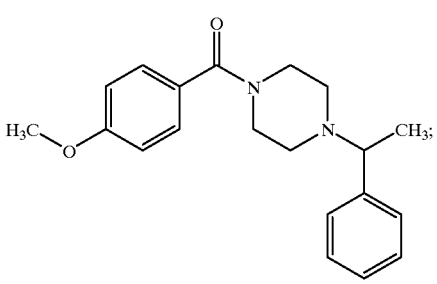
45)
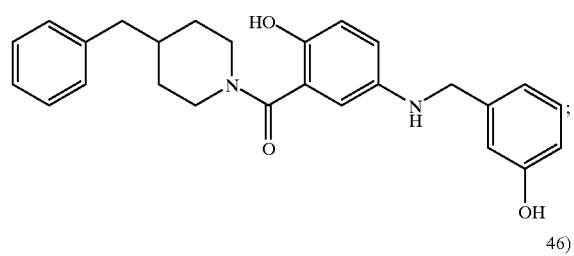
46)
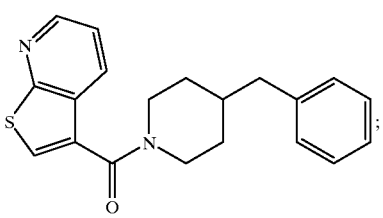

47) 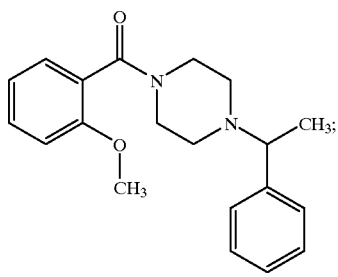
48) 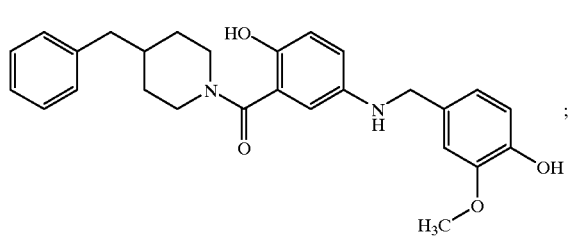
49) 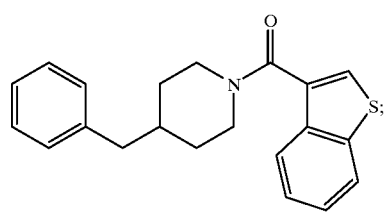
50) 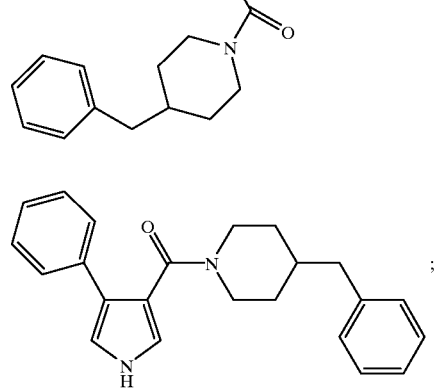
51) 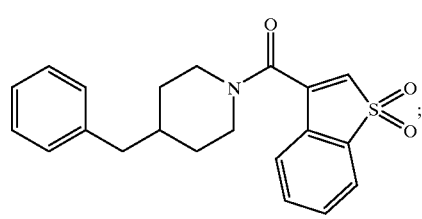
52) 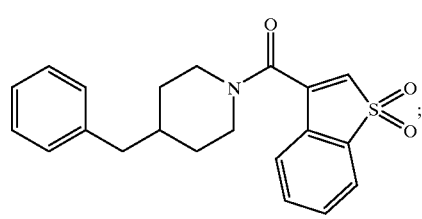
53) 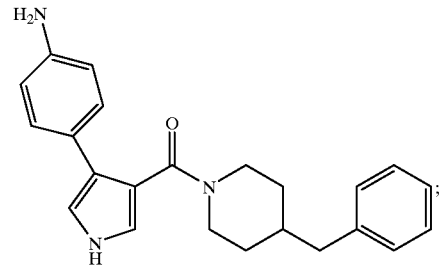
54) 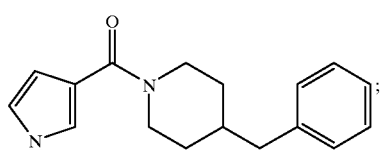
55) 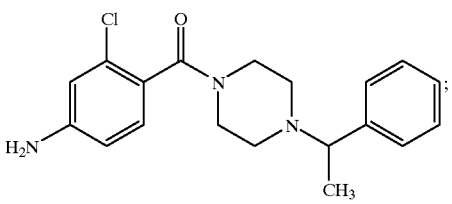
56) 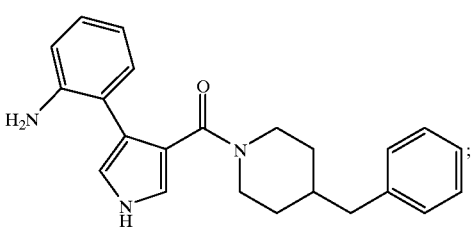
57) 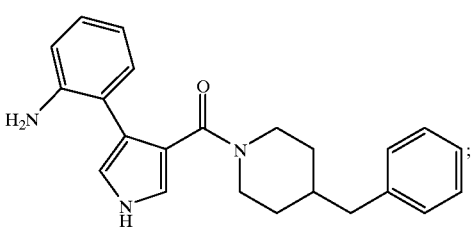
58) 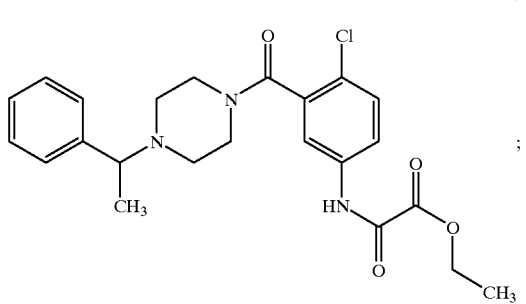

59) 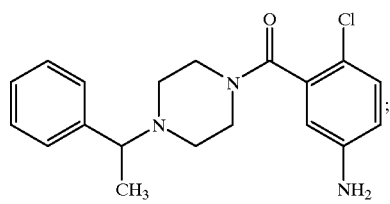
60) 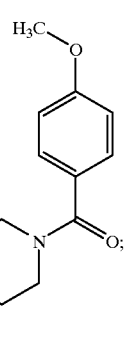 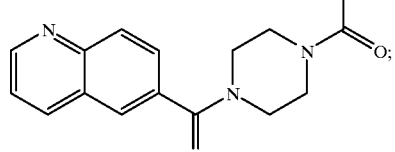
61) 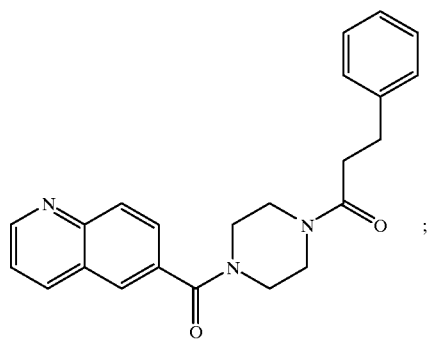
62) 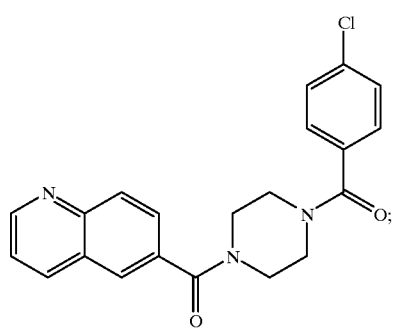
63) 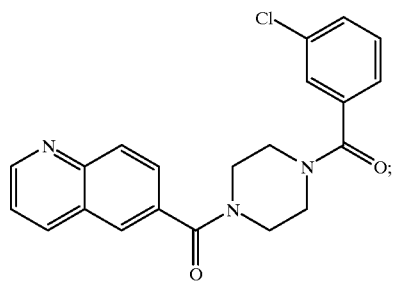
64) 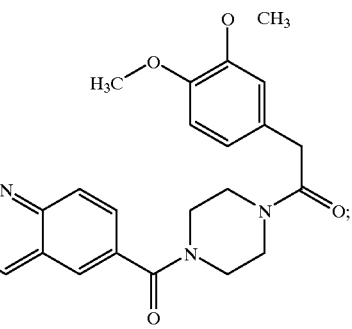
65) 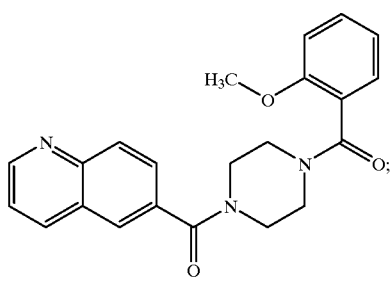
66) 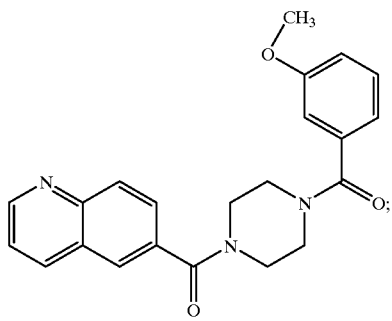
67) 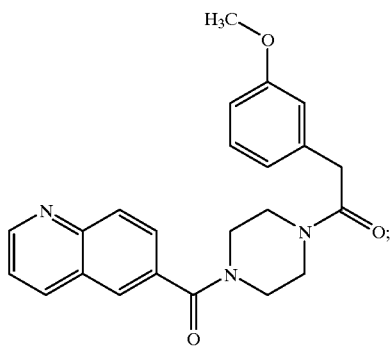
68) 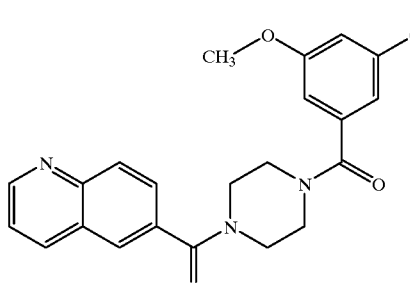

-continued

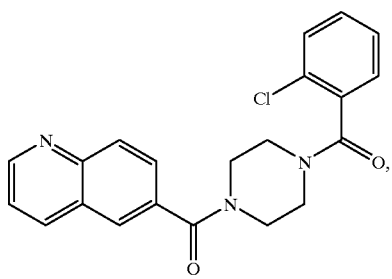
(69)

and

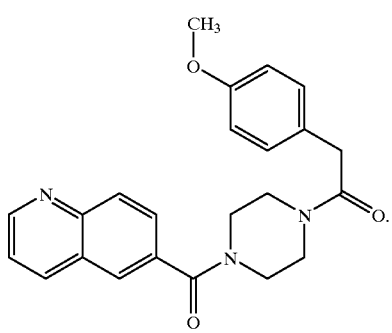
(70)

23. A pharmaceutical composition for treating conditions characterized by enhanced p38-α activity which composition comprises
a therapeutically effective amount of a compound of the formula

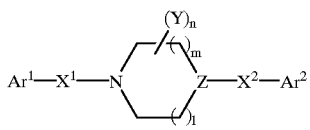
(1)

and the pharmaceutically acceptable salts thereof, or a pharmaceutical composition thereof,
wherein
Z is N or $CR^1$,
wherein $R^1$ is selected from the group consisting of optionally substituted alkyl, alkoxy, aryl, arylalkyl, aryloxy, heteroaryl, amino, ureayl, carbamate, polyhaloalkoxy, halogen, acyl, carboxy, and hydroxy, each of $X^1$ and $X^2$ is a linker,
wherein each said linker is independently saturated or unsaturated alkylene optionally containing 1–4 carbonyl, 1–4 $SO_2$, and/or 1–3 heteroatoms, including a linker which is itself CO, $SO_2$, SO or is itself a heteroatom, and said alkylene or suitable heteroatom optionally substituted with a substituent selected from the group consisting of halo, alkyl, alkoxy, cycloalkyl, aryl, aryloxy, arylalkyl, haloalkyl, polyhaloalkyl, haloalkoxy, polyhaloalkoxy, cycloheteroalkyl, cycloheteroalkylalkyl, heteroaryl, heteroarylalkyl, heteroaryloxy, arylthio, arylsulfinyl, arylsulfonyl, heteroarylthio, heteroarylsulfinyl, heteroarylsulfonyl, alkylaminocarbonyl, arylaminocarbonyl, heteroarylaminocarbonyl, alkoxycarbonyl, aryloxycarbonyl, heteroaryloxycarbonyl, acyl, aminocarbonyl, arylcarbonyl, heteroarylcarbonyl, cyano, carboxy, hydroxy, tetrazolyl, imidazole, oxazole, triazole, and —SOR wherein R is hydroxy, alkyl, aryl, alkoxy, aryloxy, cycloalkyl, heteroaryl, heteroarylalkyl, heteroaryloxy, heteroarylalkoxy or cycloheteroalkylalkoxy, $Ar^1$ and $Ar^2$ are identical or different, and represent optionally substituted aryl groups containing one or more rings optionally including one or more heteroatoms, selected from the group of O, N and S;
wherein $Ar^1$ and $Ar^2$ do not comprise an optionally substituted indolyl substituent, and
with the proviso that when $X^2$ is $CH_2$ or an isostere thereof, $X^1$ is CO or an isostere thereof, and $Ar^2$ is optionally substituted phenyl, $Ar^1$ is other than benzimidazolyl or benzotriazolyl;
wherein Y is selected from the group consisting of optionally substituted alkyl, alkoxy, cycloalkyl, cycloheteroalkyl , aryl, cycloheteroalkyl, heteroaryl, halogen, alkylaminocarbonyl, arlyaminocarbonyl, heteroarylaminocarbonyl, acyl, carboxy, hydroxy, aminocarbonyl, arylcarbonyl, heteroarylcarbonyl, cyano, amino, and alkylamino,
wherein n is an integer from 0–4, and
wherein m is an integer from 0–4 and 1 is an integer from 0–3.

24. The composition of claim 23 which further contains an additional therapeutic agent.

25. The composition of claim 24 wherein said additional therapeutic agent is a corticosteroid, a monoclonal antibody, or an inhibitor of cell division.

* * * * *